United States Patent
Ruoslahti et al.

(10) Patent No.: US 11,571,485 B2
(45) Date of Patent: Feb. 7, 2023

(54) PEPTIDES AND ANTIBODIES FOR DETECTING CHANGES IN ALZHEIMER'S DISEASE BRAIN AND METHODS OF USE THEREOF

(71) Applicant: Sanford Burnham Prebys Medical Discovery Institute, La Jolla, CA (US)

(72) Inventors: Erkki Ruoslahti, La Jolla, CA (US); Aman Mann, La Jolla, CA (US); Pablo Scodeller, La Jolla, CA (US); Sazid Hussain, La Jolla, CA (US)

(73) Assignee: Sanford Burnham Prebys Medical Discovery Institute, La Jolla, CA (US)

( * ) Notice: Subject to any disclaimer, the term of this patent is extended or adjusted under 35 U.S.C. 154(b) by 622 days.

(21) Appl. No.: 16/349,531

(22) PCT Filed: Nov. 16, 2017

(86) PCT No.: PCT/US2017/062057
§ 371 (c)(1),
(2) Date: May 13, 2019

(87) PCT Pub. No.: WO2018/094076
PCT Pub. Date: May 24, 2018

(65) Prior Publication Data
US 2021/0299283 A1 Sep. 30, 2021

Related U.S. Application Data

(60) Provisional application No. 62/423,009, filed on Nov. 16, 2016, provisional application No. 62/578,249, filed on Oct. 27, 2017.

(51) Int. Cl.
| | |
|---|---|
| A61K 49/14 | (2006.01) |
| C07K 7/06 | (2006.01) |
| C07K 7/08 | (2006.01) |
| A61K 38/00 | (2006.01) |
| A61P 25/28 | (2006.01) |
| A61P 25/00 | (2006.01) |
| A61P 29/00 | (2006.01) |
| C07K 16/22 | (2006.01) |
| A61K 39/00 | (2006.01) |

(52) U.S. Cl.
CPC ............ *A61K 49/14* (2013.01); *A61P 25/00* (2018.01); *A61P 25/28* (2018.01); *A61P 29/00* (2018.01); *C07K 7/06* (2013.01); *C07K 7/08* (2013.01); *C07K 16/22* (2013.01); *A61K 38/00* (2013.01); *A61K 2039/505* (2013.01)

(58) Field of Classification Search
CPC ......... A61K 49/14; A61K 38/00; A61P 25/00; A61P 25/28; C07K 7/06; C07K 7/08
See application file for complete search history.

(56) References Cited

U.S. PATENT DOCUMENTS

2010/0209417 A1  8/2010  Lee et al.
2015/0320706 A1  11/2015  Imbimbo et al.

FOREIGN PATENT DOCUMENTS

WO  2005/120231 A1  12/2005

OTHER PUBLICATIONS

Galagan et al. The genome of M. acetivorans reveals extensive metabolic and physiological diversity. Genome Res Apr. 2002;12(4):532-42. doi: 10.1101/gr.223902.*
GenBank entry: AAM03859.1, retrieved from https://www.ncbi.nlm.nih.gov/protein/19914191 on Jul. 30, 2021.*
PCT/US2017/062057 International Search Report dated Mar. 13, 2018.
Liu et al. "Accumulation of Connective Tissue Growth Factor+ Cells During the Early Phase of Rat Traumatic Brain Injury." Diagonostic Pathology, Jul. 10, 2014, 9(141):1-5.
Mann et al. "A Peptide for Targeted, Systemic Delivery of Imaging and Therapeutic Compounds into Acute Brain Injuries." Nature Communications, Jun. 28, 2016, 7:1-11.
Rodriguez-Vietez et al. "Astrocytosis Precedes Amyloid Plaque Deposition in Alzheimer APPswe Transgenic Mous Brain: A Correlative Positron Emission Tomography and in Vitro Imaging Study." European Journal of Nuclear Medicine and Molecular Imaging, Apr. 17, 2015, 42:119-1132.
Wiesehan et al. "Selection of D-Amino-Acid Peptides that Bind to Alzheimer's Disease Amyloid Peptide AlphaBeta 1-42 by Mirror Image Phage Display." ChemBioChem, Aug. 4, 2003, 4:748-753.
Zhao et al. "Connective Tissue Growth Factor (CTGF) Expression in the Brain is a Downstream Effector of Insulin Resistance—Associated Promotion of Alzheimer's Disease Beta-Amyloid Nueropathology." The FASEB Journal, Sep. 26, 2005, 19:2081-2082.

* cited by examiner

*Primary Examiner* — Gregory S Emch
(74) *Attorney, Agent, or Firm* — Wagenknecht IP Law Group PC

(57) ABSTRACT

The present invention is based on the seminal discovery of a panel of targeting peptides and antibodies that can recognize AD brains at different stages of the disease, starting from early to advanced stage. The peptide probes described here are unique in the field and can be expected to advance understanding on early neurodegenerative changes associated with AD and improve the therapeutic outcomes by early detection and intervention in AD. Further, the invention provides antibodies that can be used to treat AD.

13 Claims, 10 Drawing Sheets
Specification includes a Sequence Listing.

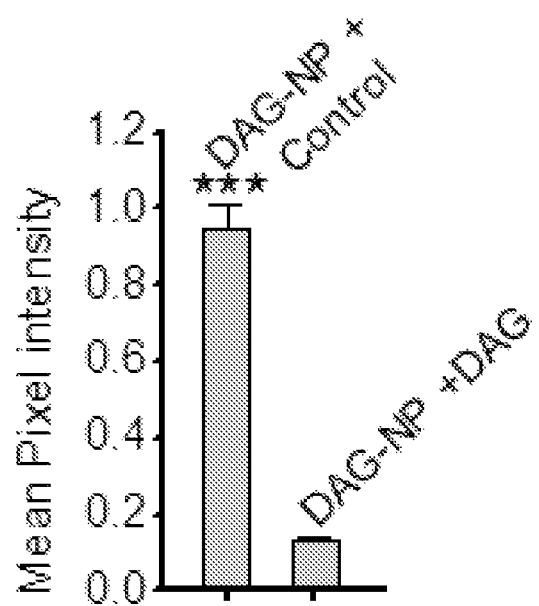
FIGURE 12B
 
FIGURE 13A  FIGURE 13B

PEPTIDES AND ANTIBODIES FOR DETECTING CHANGES IN ALZHEIMER'S DISEASE BRAIN AND METHODS OF USE THEREOF

RELATED APPLICATIONS

This application is a US national phase entry under 35 USC § 371 of international patent application no. PCT/US2017/062057, filed Nov. 16, 2017, which claims the benefit of priority under § 119(e) of U.S. Provisional Patent Application Ser. No. 62/578,249, filed on Oct. 27, 2017, and U.S. Provisional Patent Application Ser. No. 62/423,009, filed on Nov. 16, 2016. The disclosure of each of the prior applications is considered part of and is incorporated by reference in the disclosure of this application.

The official copy of the sequence listing is submitted electronically via EFS-Web as an ASCII formatted file as U.S. Ser. No. 16/349,531 SEQ ID created on 24 Sep. 2019 and having a size of 25 Kilobytes. The sequence listing contained in this ASCII formatted document forms part of the specification and is herein incorporated by reference in its entirety.

INCORPORATION OF SEQUENCE LISTING

The material in the accompanying sequence listing is hereby incorporated by reference into this application. The accompanying sequence listing text file, name BURN1730_1WO_Sequence_Listing, was created on Nov. 16, 2017, and is 25 kb. The file can be assessed using Microsoft Word on a computer that uses Windows OS

BACKGROUND

Field of the Invention

The invention relates generally to detecting and treating disease, and more specifically to detection and treatment of neuroinflammatory disorders and/or neurodegenerative disorders, such as Alzheimer's disease (AD).

Background Information

AD is the most common progressive neurodegenerative disorder associated with aging. As life expectancy increases in the US and other developed nations, this disease will reach epidemic proportions by the year 2050 with far reaching economic implications. The prevalent hypothesis regarding AD pathogenesis is based on the premise that deposition of amyloid-β peptide (Aβ), followed by hyperphosphorylated tau deposits, plays a key role in neurodegeneration and brain atrophy in AD. However, failure to predict clinical efficacy by targeting Aβ in recent clinical trials, dictates the necessity of identifying additional cellular pathways, processes, and molecules involved in AD pathogenesis for diagnosis and treatment to improve clinical outcomes.

Cerebrovascular changes in AD animal models and human patients have been reported. These morphological and functional changes can contribute to neuronal dysfunction and neurodegeneration. For instance, degeneration of blood-brain barrier (BBB)-associated pericytes can lead to impairment of the BBB, resulting in serum buildup of proteins and edema, increase in reactive oxygen species, and neuronal injury. However, this disruption in microvascular integrity also provides a therapeutic opportunity to access the brain extravascular space from the systemic circulation for delivering therapeutics and imaging agents to the AD brain.

There exists a need for improved techniques for discovering markers of AD, as well as utilizing such markers to selectively target molecules into pathological sites of the AD brain.

SUMMARY

The present invention is based on the seminal discovery of a panel of targeting peptides and antibodies that can recognize AD brains at different stages of the disease, starting from early to advanced stage. The peptide probes described here are unique in the field and can be expected to advance understanding on early neurodegenerative changes associated with AD and improve the therapeutic outcomes by early detection and intervention in AD. The antibodies described here may be used as diagnostic or therapeutic agent for the treatment of AD.

Accordingly, the present disclosure provides an isolated peptide. In embodiments, the peptide includes an amino acid sequence as set forth in any one of SEQ ID NOs: 2-100. In some embodiments, the peptide includes an amino acid sequence having a sequence motif $(X)_n X_1 X_2 X_3 X_4 (X)_n$ (SEQ ID NO: 1), wherein X is any amino acid, n is 0 to 8 amino acids, $X_1$ is G or A, $X_2$ is K, H or R, $X_3$ is K, H or R, and $X_4$ is N or Q. In one embodiment, the peptide includes the sequence motif $(X)_n GRKQ(X)_n$ (SEQ ID NO: 104), wherein X is any amino acid, and wherein n is 0 to 8 amino acids. In embodiments, the peptide has an amino acid sequence as set forth in SEQ ID NO: 3 (CASPRLSKC), SEQ ID NO: 11 (CESPLLSEC), or SEQ ID NO: 102 (CDAGRKQKC); also herein referred to as "DAG"). In various embodiments, the peptide is operatively linked to a therapeutic agent or detection moiety.

The present disclosure also provides a nucleic acid sequence encoding the peptide of the disclosure.

Further, the present disclosure provides an expression vector including the nucleic acid sequence of the disclosure, as well as an isolated cell including the expression vector.

A phage including the peptide of the disclosure is also provided.

The disclosure additionally provides a method for detecting a protein. The method includes contacting brain tissue from a subject having or suspected of having AD with one or more peptides of the disclosure; and detecting binding of the peptide to the brain tissue.

The disclosure further provides a method for detecting AD, or progression of AD in a subject. The method includes contacting brain tissue from a subject having or suspected of having AD with one or more peptides of the disclosure; and detecting binding of the peptide to the brain tissue. The method optionally further includes assessing a disease state based on the binding.

Also provided is a method of screening for a peptide which preferentially binds brain tissue from a subject having, or at risk of having, AD. The method includes: a) generating a phage library comprising at least one discrete phage member displaying a putative binding peptide; b) contacting brain tissue having characteristics of AD with the at least one discrete phage member; and c) detecting binding of the putative binding peptide to the brain tissue.

The disclosure also provides a method of treating AD in a subject. The method includes administering to the subject a peptide of the disclosure operably linked to, or in combination with, a therapeutic agent, thereby treating the AD.

The disclosure further provides a method of imaging brain tissue having, or suspected of having AD. The method includes: a) contacting the brain tissue with a peptide of the disclosure, wherein the peptide is operatively linked to a detection moiety; and b) generating an image of the brain tissue, thereby imaging the brain tissue. In embodiments, the peptide is conjugated to fluorescamine.

The disclosure also provides a pharmaceutical composition including a peptide of the disclosure operably linked to, or in combination with, a therapeutic agent, and a pharmaceutically acceptable carrier.

The disclosure further provides a kit including a peptide of the disclosure and one or more reagents for detecting binding of the peptide to brain tissue.

The disclosure provides methods of treating a neuroinflammatory disorder and/or neurodegenerative disorder in a subject, comprising administering to the subject an anti-connective tissue growth factor (CTGF) antibody or antigen binding fragment thereof, thereby treating the neuroinflammatory disorder and/or neurodegenerative disorder in the subject. In one embodiment, neuroinflammatory disorder and/or neurodegenerative disorder is Alzheimer's disease, Parkinson's disease, multiple sclerosis, amyotrophic lateral sclerosis (ALS), myasthenia gravis, chronic demyelinating polyneuropathy, Charcot Marie Tooth syndrome, neuromyelitis optica, optic neuritis, diffuse cerebral sclerosis, Shilder's encephalitis periaxialis diffusa, Huntington's Disease, Balo's concentric sclerosis, progressive supranuclear palsy, transverse myelitis, acute disseminated encephalomyelitis, necrotizing hemorrhagic encephalitis, leukodystrophies, CNS injury, stroke, age-related dementia, depression, bipolar disorder, Guillain-Bane syndrome, dementia, frontotemporal dementia, vascular dementia or chronic inflammatory demyelinating polyneuropathy (CIDP). In another embodiment, the neuroinflammatory disorder and/or neurodegenerative disorder is Alzheimer's disease and the subject is human. In certain embodiments, the antibodies and antigen binding fragments may be administered by intravenous, oral, intramuscular, subcutaneous or intrathecal administration. In some embodiments, an additional therapeutic agent is administered. In specific embodiments, the additional therapeutic agent is donepezil, rivastigmine, galantamine, memantine or a combination thereof. In additional embodiments, the antibodies or antigen binding fragments are conjugated to a toxic agent. In specific embodiments, the toxic agent is a cytotoxic agent, a cytokine, an anti-angiogenic agent, a chemotherapeutic agent, a pro-apoptosis agent, an enzyme, a hormone, a growth factor, a peptide, a protein, an antibiotic, an antibody, a Fab fragment of an antibody, an antigen, a survival factor, an anti-apoptotic agent, a hormone antagonist, a virus, a bacteriophage, a bacterium, a liposome, a cell, a nucleic acid or an expression vector. In further embodiments, the antibodies or antigen binding fragments are detectably labeled.

The disclosure also provides methods of imaging brain tissue of a subject comprising contacting the brain tissue with an anti-CTGF antibody or antigen binding fragment thereof; and generating an image of the brain tissue. In one embodiment the imaging is PET or MRI imaging and the antibody or antigen binding fragment is detectably labeled.

The disclosure additionally provides methods of treating a neuroinflammatory disorder and/or neurodegenerative disorder comprising contacting brain tissue with an anti-CTGF antibody or antigen binding fragment thereof in a subject in need thereof. In one embodiment, the brain tissue is in the hippocampus and the subject is human. In another embodiment, neuroinflammatory disorder and/or neurodegenerative disorder is Alzheimer's disease, Parkinson's disease, multiple sclerosis, amyotrophic lateral sclerosis (ALS), myasthenia gravis, chronic demyelinating polyneuropathy, Charcot Marie Tooth syndrome, neuromyelitis optica, optic neuritis, diffuse cerebral sclerosis, Shilder's encephalitis periaxialis diffusa, Huntington's Disease, Balo's concentric sclerosis, progressive supranuclear palsy, transverse myelitis, acute disseminated encephalomyelitis, necrotizing hemorrhagic encephalitis, leukodystrophies, CNS injury, stroke, age-related dementia, depression, bipolar disorder, Guillain-Bane syndrome, dementia, frontotemporal dementia, vascular dementia or chronic inflammatory demyelinating polyneuropathy (CIDP). In a specific embodiment, the neuroinflammatory disorder and/or neurodegenerative disorder is Alzheimer's disease. In an additional embodiment, an additional therapeutic agent is administered and the additional therapeutic agent is donepezil, rivastigmine, galantamine, memantine or a combination thereof or any of the peptides previously described. In further embodiments, the antibody or antigen binding fragment is conjugated to a toxic agent and/or is detectably labeled.

The disclosure further provides a method of diagnosing, prognosing, or determining progression of a neuroinflammatory disorder and/or neurodegenerative disorder in a subject, or predicting benefit from therapy in a subject having a neuroinflammatory disorder and/or neurodegenerative disorder in a subject, comprising contacting brain tissue in the subject with an anti-CTGF antibody or antigen binding fragment; and diagnosing, prognosing, or determining progression of the neuroinflammatory disorder and/or neurodegenerative disorder or predicting benefit from therapy in the subject. In certain embodiments, the brain tissue is the hippocampus and the neuroinflammatory disorder and/or neurodegenerative disorder is Alzheimer's disease. In another embodiment, the subject is human. In some embodiments, an additional therapeutic agent, such as donepezil, rivastigmine, galantamine, memantine or a combination thereof is administered. In another embodiment, the brain tissue is imaged by PET or MM imaging. In an additional embodiment, the antibody or antigen binding fragment is conjugated to a toxic agent and/or is detectably labeled. In a further embodiment, prognosing or determining progression of Alzheimer's disease comprises determining the expression level of glial fibrillary acidic protein (GFAP) in the hippocampus. The determining the expression level of GFAP may comprise imaging the brain tissue.

BRIEF DESCRIPTION OF THE DRAWINGS

FIG. 1A depicts phage titration of recovered phage from AD and WT hippocampus (A) and high throughput sequencing of the phage inserts.

FIG. 1B relates to phage titration showing that about 5 times more phage were recovered from the AD hippocampus than from the normal control. In the sequencing, phages displaying the peptides code named CASP (SEQ ID NO: 3; CASPRLSKC), CES (SEQ ID NO: 11, CESPLLSEC), and DAG (SEQ ID NO: 102, CDAGRKQKC) dominated. Hippocampus from age-matched normal wild-type mouse brain was used as a control.

FIG. 5A is a schematic representation of phage screening done in transgenic hAPP-J20 tg mice. A $CX_7C$ library ($10^9$ pfu) was injected intravenously in hAPP-J20 mice and wild-type (WT) littermate controls of different ages. After 30 minutes of circulation and perfusion to remove unbound phage, the hippocampus was excised and phages were recovered and quantified. FIG. 5B is a graph showing the quantification.

FIG. 9A depicts data from Tg2576 and WT mice. FIG. 9B depicts data from hAPP-J20 and WT mice. Frozen brain sections from Tg2576 and WT (A) mice and hAPP-J20 and WT (B) mice were stained for CTGF (green) and counterstained with DAPI. Green signal was analyzed by fluorescence microscopy and quantified from the hippocampus and cortex regions of the Tg and the WT mice. Scale bar: 200 µm. *$P<0.05$, **$P<0.01$.

FIGS. 12A-12B is a graphical representation pertaining to DAG-AgNPs binding to cells derived from AD patient derived iPS cells. FIG. 12A is a graph depicting binding data. Human iPS cells derived from an AD patient were differentiated into brain endothelial-like cells and these cells were used in an overlay assay with AgNPs coated with FAM-DAG. AgNPs coated with a FAM-labeled inert peptide serves as a control. Fluorescent microscopy analysis of native FAM fluorescence (green) was used to observe AgNP binding, and the binding was quantified using ImageJ™ software (bar graph). FIG. 12B is a graph depicting binding data. The cells were incubated with DAG-AgNPs together with 200 µM of free, non-labeled control peptide or non-labeled DAG. Fluorescent microscopy analysis of native FAM fluorescence (green) was used to observe AgNP binding, and the binding was quantified using ImageJ™ software (bar graph). Free DAG peptide significantly inhibits the binding of the AgNPs, indicating specificity of the binding.

FIGS. 13A-13B show a MRI image of J20 mice. Ex vivo imaging of perfused brains from these mice revealed punctate signal (asterisk) in the hippocampus in AD animal (A), which was absent in the wild-type animal (B) in T2* imaging.

DETAILED DESCRIPTION

Figure 1A:
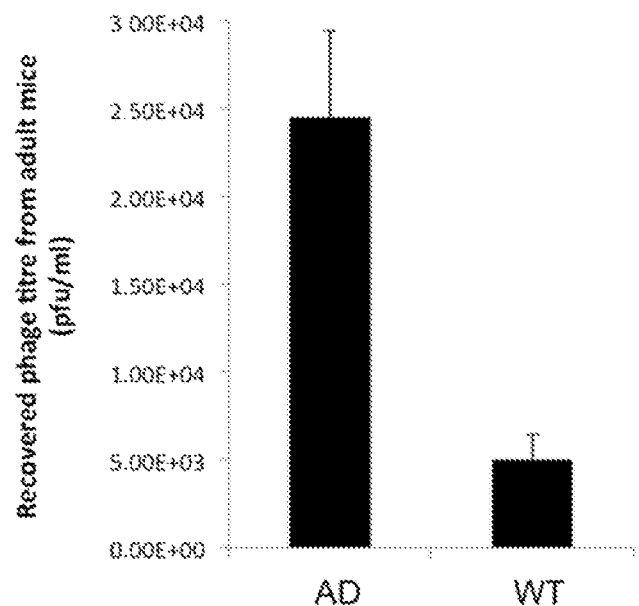
FIGS. 1A-1B is a graphical representation depicting data relating to screening of phage homing to AD hippocampus.

In vivo peptide phage display can be used for unbiased probing of tissues in situ for specific molecular signatures, particularly in the vasculature. Given the changes reported in the neurovascular unit in AD, in vivo phage display was conducted to identify peptides that would specifically recognize molecular changes associated with AD pathogenesis, and enable targeting of such sites from systemic administration. Additionally, antibodies described here specifically recognize molecular changes associated with AD pathogenesis and may be useful agents for the diagnosis and treatment of AD.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

A new approach was taken to AD, searching for previously unknown markers for the disease by using phage library screening. An in vivo phage library screening was developed to probe molecular specificities in the vasculature. This approach has been successfully utilized to probe the in situ environment of tumors and some other pathologies. In vivo phage peptide library screens were conducted to probe for signatures in AD brain. Given that AD includes a vascular component, it was determined that the vasculature in AD expresses specific markers.

The screens discussed herein employed a transgenic rodent model of AD. The characteristics desired in the peptides were specificity for AD versus normal brain (and ultimately with regard to brain diseases other than AD), recognition of AD at the earliest stages of the disease, abundance of peptide accumulation in the brain, and ability to recognize human AD. An additional desirable characteristic was recognition of an AD marker on endothelial cells because of the availability of the blood vessels to circulating probes regardless of the status of the blood-brain barrier (BBB).

Through this approach, the inventors have identified a panel of targeting peptides that can recognize AD brains at different stages of the disease, starting from early to advanced stage. The peptide probes described here are unique in the field and can be expected to advance understanding of early neurodegenerative changes associated with AD and improve the therapeutic outcomes by early detection and intervention in AD.

Accordingly, the disclosure provides an isolated peptide that binds AD brain tissue. In embodiments, the peptide includes an amino acid sequence having a sequence motif set forth as follows:

$(X)_n X_1 X_2 X_3 X_4 (X)_n$ (SEQ ID NO: 1), wherein X is any amino acid, n is 0 to 8 amino acids, $X_1$ is G or A, $X_2$ is K, H or R, $X_3$ is K, H or R, and $X_4$ is N or Q.

In one embodiment, the peptide includes a sequence motif set forth as follows:

$(X)_n GRKQ(X)_n$ (SEQ ID NO: 104), wherein X is any amino acid, and wherein n is 0 to 8 amino acids.

For example, in one embodiment, the peptide has an amino acid sequence as set forth in SEQ ID NO: 102 (CDAGRKQKC; also herein referred to as "DAG").

In various embodiments, the peptide includes an amino acid sequence as set forth in any one of SEQ ID NOs: 2-100 (see Table 1 of Example 1).

"Polypeptide(s)," "peptide(s)" and "protein(s)" are used interchangeably herein to refer to a polymer of amino acid residues. The terms apply to naturally occurring amino acid polymers, as well as, amino acid polymers in which one or more amino acid residues is an artificial chemical mimetic of a corresponding naturally occurring amino acid, i.e., a non-naturally occurring amino acid.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

In various embodiments, the peptide of the disclosure includes one or more non-naturally occurring amino acids.

"Conservatively modified variants" applies to both nucleic acid and amino acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "isolated" or "substantially purified," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

Peptides of the present disclosure, may be of any suitable length. For example, one of skill in the art would understand what length is suitable for allowing the peptide to contact brain tissue regardless of the BBB. Such molecules are typically from about 3 to 20, 4 to 18, 4 to 16, 4 to 12, 4 to 10, 4 to 9, 4 to 8, 4 to 7, or 4 to 6 amino acid residues in length. For example the molecule may be about 3, 4, 5, 6, 7, 8, 9, 10, 11, 12, 13, 14, 15, 16, 17, 18, 19 or 20 amino acid residues in length. Such peptides may include from at least about 3 to more than about 20 amino acids, including at least about 3 amino acid residues, at least about 4 amino acid residues, at least about 5 amino acid residues, at least about 6 amino acid residues, at least about 7 amino acid residues, at least about 8 amino acid residues, at least about 9 amino acid residues, at least about 10 amino acid residues, at least about 11 amino acid residues, at least about 12 amino acid residues, at least about 13 amino acid residues, at least about 14 amino acid residues, at least about 15 amino acid residues, at least about 16 amino acid residues, at least about 17 amino acid residues, at least about 18 amino acid residues, at least about 19 amino acid residues, at least about 20 amino acid residues or greater than 20 amino acid residues.

The present disclosure also provides a nucleic acid sequence encoding the peptide of the disclosure.

The term "polynucleotide" or "nucleotide sequence" or "nucleic acid molecule" is used broadly herein to mean a sequence of two or more deoxyribonucleotides or ribonucleotides that are linked together by a phosphodiester bond. As such, the terms include RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the terms as used herein include naturally occurring nucleic acid molecules, which can be isolated from a cell, as well as synthetic polynucleotides, which can be prepared, for example, by methods of chemical synthesis or by enzymatic methods such as by the polymerase chain reaction (PCR). It should be recognized that the different terms are used only for convenience of discussion so as to distinguish, for example, different components of a composition.

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. Depending on the use, however, a polynucleotide also can contain nucleotide analogs, including non-naturally occurring synthetic nucleotides or modified naturally occurring nucleotides. Nucleotide analogs are well known in the art and commercially available, as are polynucleotides containing such nucleotide analogs. The covalent bond linking the nucleotides of a polynucleotide generally is a phosphodiester bond. However, depending on the purpose for which the polynucleotide is to be used, the covalent bond also can be any of numerous other bonds, including a thiodiester bond, a phosphorothioate bond, a peptide-like bond or any other bond known to those in the art as useful for linking nucleotides to produce synthetic polynucleotides.

A polynucleotide or oligonucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template.

The nucleic acids encoding the peptides of the invention can also be generated by direct chemical synthesis using methods such as the phosphotriester method; the phosphodiester method; the diethylphosphoramidite method; and the solid support method of U.S. Pat. No. 4,458,066. If the DNA sequence is synthesized chemically, a single stranded oligonucleotide will result. This may be converted into double stranded DNA by hybridization with a complementary sequence, or by polymerization with a DNA polymerase using the single strand as a template.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Further, the present disclosure provides an expression vector including the nucleic acid sequence of the disclosure, as well as an isolated cell including the expression vector. To obtain high level expression of a cloned gene or nucleic acid, one typically subclones a nucleic acid encoding the peptide into an expression vector that contains an appropriate promoter to direct transcription, a transcription/translation terminator, and if for a nucleic acid encoding a peptide, a ribosome binding site for translational initiation. Suitable bacterial promoters are well known in the art and described, e.g., in Sambrook et al. and Ausubel et al. Bacterial expression systems for expressing protein are available in, e.g., E. coli, Bacillus sp., and Salmonella (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein to be expressed and signals required for efficient polyadenylation of the transcript, ribosome binding sites, and translation termination. The nucleic acid sequence encoding a protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., Nature (1977) 198: 1056), the tryptophan (trp) promoter system (Goeddel et al., Nucleic Acids Res. (1980) 8: 4057), the tac promoter (DeBoer, et al., Proc. Natl. Acad. Sci. U.S.A. (1983) 80:21-25); and the lambda-derived $P_L$ promoter and N-gene ribosome binding site (Shimatake et al., Nature (1981) 292: 128). The particular promoter system is not critical to the invention, any available promoter that functions in prokaryotes can be used.

Standard bacterial expression vectors include plasmids such as pBR322-based plasmids, e.g., pBLUESCRIPT™, pSKF, pET23D, λ-phage derived vectors, and fusion expression systems such as GST and LacZ. Epitope tags can also be added to recombinant proteins to provide convenient methods of isolation, e.g., c-myc, HA-tag, 6-His tag (SEQ ID NO:124), maltose binding protein, VSV-G tag, anti-DYKDDDDK tag (SEQ ID NO:125), or any such tag, a large number of which are well known to those of skill in the art.

Eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook and Russell, supra). It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of the protein, which is recovered from the culture using standard techniques identified below.

Accordingly, the present disclosure provides an isolated cell including the expression vector of the disclosure.

Once expressed, the peptides of the disclosure can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

In addition to recombinant methods, the peptides of the disclosure can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. J. Am. Chem. Soc. 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N,N'-dicycylohexylcarbodiimide) are known to those of skill.

One embodiment of the present invention provides a conjugate peptide including a peptide of the invention, operatively linked to an effector molecule or detectable label. In embodiments, the effector molecule may include a therapeutic molecule, for example, a prodrug, a small molecule, a biomolecule, such as a peptide, an oligonucleotide (e.g., DNA, RNA, mRNA, miRNA, siRNA, sgRNA, antisense or sense, and the like), a lipid, and the like.

As such, the disclosure also provides a method of treating AD in a subject. The method includes administering to the subject a peptide of the disclosure operably linked to, or in combination with, an effector molecule, such as a therapeutic agent, thereby treating the AD.

The terms "administration" or "administering" are defined to include an act of providing a compound and/or therapeutic agent and/or peptide of the invention to a subject in need of treatment. Administration may be via any appropriate route, depending on the type of therapeutic.

The effector molecule and the peptide may be conjugated by chemical or by recombinant means as described herein. Chemical modifications include, for example, derivatization for the purpose of linking the effector molecule and the peptide to each other, either directly or through a linking compound, by methods that are well known in the art of protein chemistry. Both covalent and noncovalent attachment means may be used with the humanized antibodies of the present invention.

The procedure for attaching an effector molecule to a peptide will vary according to the chemical structure of the moiety to be attached to the peptide. Polypeptides typically contain a variety of functional groups; e.g., carboxylic acid (COOH), free amine (—$NH_2$) or sulfhydryl (—SH) groups, which are available for reaction with a suitable functional group on a peptide to result in the binding of the effector molecule.

Alternatively, the peptide is derivatized to expose or to attach additional reactive functional groups. The derivatization may involve attachment of any of a number of linker molecules such as those available from Pierce Chemical Company, Rockford Ill.

The linker is capable of forming covalent bonds to both the peptide and to the effector molecule. Suitable linkers are well known to those of skill in the art and include, but are not limited to, straight or branched-chain carbon linkers, heterocyclic carbon linkers, or peptide linkers. Where the peptide and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the peptide when the conjugate has reached its target site. Therefore, in these circumstances, conjugates will comprise linkages that are cleavable in the vicinity of the target site. Cleavage of the linker to release the effector molecule from the peptide may be prompted by enzymatic activity or conditions to which the conjugate is subjected either inside the target cell or in the vicinity of the target site.

In one conjugation embodiment, the means of linking the effector molecule and the peptide comprises a heterobifunctional coupling reagent which ultimately contributes to formation of an intermolecular disulfide bond between the effector molecule and the peptide. Other types of coupling reagents that are useful in this capacity for the present invention are described, for example, in U.S. Pat. No. 4,545,985. Alternatively, an intermolecular disulfide may conveniently be formed between cysteines in the effector molecule and the peptide which occur naturally or are inserted by genetic engineering. The means of linking the effector molecule and the peptide may also use thioether linkages between heterobifunctional crosslinking reagents or specific low pH cleavable crosslinkers or specific protease cleavable linkers or other cleavable or noncleavable chemical linkages. The means of linking the effector molecule and the peptide may also comprise a peptidyl bond formed between the effector molecule and the peptide which are separately synthesized by standard peptide synthesis chemistry or recombinant means.

Exemplary chemical modifications of the effector molecule and the peptide of the present invention also include derivitization with polyethylene glycol (PEG) to extend time of residence in the circulatory system and reduce immunogenicity, according to well-known methods (See for example, Lisi, et al., Applied Biochem. 4:19 (1982); Beauchamp, et al., Anal Biochem. 131:25 (1982); and Goodson, et al., Bio/Technology 8:343 (1990)).

Peptides of the present invention may optionally be covalently or non-covalently linked to a detectable label or moiety. Detectable labels/moieties suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

In embodiments, the detection moiety is luciferase (LUC), β-lactamase, chloramphenicol acetyltransferase (CAT), adenosine deaminase (ADA), aminoglycoside phosphotransferase (neo, G418), dihydrofolate reductase (DHFR), hygromycin-B-phosphotransferase (HPH), thymidine kinase (TK), β-galactosidase (β-gal), and xanthine guanine phophoribosyltransferase (XGPRT), an affinity or epitope tag, or a fluorescent protein.

In one embodiments, the detection moiety is fluorescamine.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

As such, the disclosure further provides a method of imaging brain tissue having, or suspected of having AD. The method includes: a) contacting the brain tissue with a peptide of the disclosure, wherein the peptide is operatively linked to a detection moiety; and b) generating an image of the brain tissue, thereby imaging the brain tissue. In a preferred embodiments, the peptide is conjugated to fluorescamine.

The present disclosure further provides a method for detecting a protein. The method includes contacting brain tissue from a subject having or suspected of having AD with one or more peptides of the disclosure; and detecting binding of the peptide to the brain tissue.

The disclosure further provides a method for detecting AD, or progression of AD in a subject. The method includes contacting brain tissue from a subject having or suspected of having AD with one or more peptides of the disclosure; and detecting binding of the peptide to the brain tissue. The method optionally further includes assessing a disease state based on the binding, for example classifying disease progression. The method may further include providing a prognosis or diagnostic information to the subject. The method may further include treating administering a therapeutic agent to the subject, for example, a peptide conjugate of the disclosure including a therapeutic.

"Diagnosing" includes determining, monitoring, confirmation, subclassification, and prediction of the relevant disease, complication, or risk. "Determining" relates to becoming aware of a disease, complication, risk, and the like. "Monitoring" relates to keeping track of an already diagnosed disease, complication, or risk factor, e.g., to analyze the progression of the disease or the influence of a particular treatment on the progression of disease or complication. "Confirmation" relates to the strengthening or substantiating of a diagnosis already performed using other indicators or markers. "Classification" or "subclassification" relates to further defining a diagnosis according to different subclasses of the diagnosed disease, disorder, or condition, e.g., defining according to mild, moderate, or severe forms of the disease or risk. "Prediction" relates to prognosing a disease, disorder, condition, or complication before other symptoms or markers have become evident or have become significantly altered.

The term "risk" relates to the possibility or probability of a particular event occurring either presently, or, at some point in the future. "Risk stratification" refers to an arraying of known clinical risk factors to allow physicians to classify patients into a low, moderate, high or highest risk of developing of a particular disease, disorder, or condition.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The invention further provides a method for determining susceptibility of a subject to a therapeutic regime to treat AD, or monitoring progression of AD in a subject by administering a peptide of the disclosure linked to or in combination with a detection moiety and detecting binding of the peptide in brain tissue.

In various embodiments, assessments be made over a particular time course in various intervals to assess a subject's progression and pathology. For example, analysis may be performed at regular intervals such as one day, two days, three days, one week, two weeks, one month, two months, three months, six months, or one year, in order to track level tumor progression or regression as a function of time. In the case of existing AD patients, this provides a useful indication of the progression of the disease and assists medical practitioners in making appropriate therapeutic choices.

Detection and diagnosis methods generally include use of peptide of the disclosure operatively linked to a detection moiety as described herein. Detection of binding may be accomplished by any technique suitable for the detection moiety utilized. For example, use of a fluorescent label would entail use of imaging techniques to detect binding.

As used herein, "providing a diagnosis" or "diagnostic information" refers to any information that is useful in determining whether a patient has a disease or condition and/or in classifying the disease or condition into a phenotypic category or any category having significance with regards to the prognosis of or likely response to treatment (either treatment in general or any particular treatment) of the disease or condition. Similarly, diagnosis refers to providing any type of diagnostic information, including, but not limited to, whether a subject is likely to have a condition (such as a AD), information related to the nature or classification of a tissue lesion associated with AD, information related to prognosis and/or information useful in selecting an appropriate treatment. Selection of treatment can include the choice of a particular therapeutic agent or other treatment modality.

As used herein, the terms "providing a prognosis", "prognostic information", or "predictive information" refer to providing information regarding the impact of the presence of AD (e.g., as determined by the diagnostic methods of the present invention) on a subject's future health (e.g., expected morbidity or mortality, and the likelihood of getting AD).

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject can visit a medical center to have the sample obtained and sent to the profiling center, or subjects can collect the sample themselves and directly send it to a profiling center. Where the sample comprises previously determined biological information, the information can be directly sent to the profiling service by the subject (e.g., an information card containing the information can be scanned by a computer and the data transmitted to a computer of the profiling center using an electronic communication system). Once received by the profiling service, the sample is processed and a profile is produced (e.g., expression data), specific for the diagnostic or prognostic information desired for the subject.

The profile data is then prepared in a format suitable for interpretation by a treating clinician. For example, rather than providing raw expression data, the prepared format can represent a diagnosis or risk assessment for the subject, along with recommendations for particular treatment options. The data can be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject can chose further intervention or counseling based on the results. In some embodiments, the data is used for research purposes. For example, the data can be used to further optimize the inclusion or elimination of markers as useful indicators of a particular condition or stage of disease.

In yet other embodiments, the present invention provides kits for the detection and characterization of AD. In some embodiments, the kits contain a peptide of the disclosure linked to or in combination with a detection moiety, in addition to detection reagents and buffers. In some embodiments, the kits contain all of the components necessary and/or sufficient to perform a detection assay, including all controls, directions for performing assays, and any necessary software for analysis and presentation of results.

Also provided is a method of screening for a peptide which preferentially binds brain tissue from a subject having, or at risk of having, AD. The method includes: a) generating a phage library comprising at least one discrete phage member displaying a putative binding peptide; b) contacting brain tissue having characteristics of AD with the at least one discrete phage member; and c) detecting binding of the putative binding peptide to the brain tissue.

A "phage display library" refers to a "library" of bacteriophages on whose surface is expressed exogenous peptides or proteins. The foreign peptides or polypeptides are displayed on the phage capsid outer surface. The foreign peptide can be displayed as recombinant fusion proteins incorporated as part of a phage coat protein, as recombinant fusion proteins that are not normally phage coat proteins, but which are able to become incorporated into the capsid outer surface, or as proteins or peptides that become linked, covalently or not, to such proteins. This is accomplished by inserting an exogenous nucleic acid sequence into a nucleic acid that can be packaged into phage particles. Such exogenous nucleic acid sequences may be inserted, for example, into the coding sequence of a phage coat protein gene. If the foreign sequence is cloned in frame, the protein it encodes will be expressed as part of the coat protein. Thus, libraries of nucleic acid sequences, such as $CX_7C$ peptides, can be so inserted into phages to create "phage libraries." As peptides and proteins representative of those encoded for by the nucleic acid library are displayed by the phage, a "peptide-display library" is generated. While a variety of bacteriophages are used in such library constructions, typically, filamentous phage are used (Dunn (1996) Curr. Opin. Biotechnol. 7:547-553).

In embodiments, the screening method utilizes a T7 phage library expressing random peptides with the composition of $CX_nC$ (C=cysteine; X=any amino acid; n=7). However, n may vary from about 3 to 20. For example, n may be from about 3 to 20, 4 to 18, 4 to 16, 4 to 12, 4 to 10, 4 to 9, 4 to 8, 4 to 7, or 4 to 6. In embodiments, n is 3, 4, 5, 6, 7, 8, 9, 10, 11, 12, 13, 14, 15, 16, 17, 18, 19 or 20.

The disclosure also provides a pharmaceutical composition including a peptide of the disclosure operably linked to, or in combination with, an effector molecule, such as a therapeutic agent, and a pharmaceutically acceptable carrier.

The pharmaceutical compositions of the invention are useful for systemic or parenteral administration, such as intravenous administration or administration into a body cavity.

The compositions for administration will commonly comprise a solution of the peptide or peptide conjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp.315-339, (1992) both of which are incorporated herein by reference.

Polymers can be used for ion-controlled release of compositions of the present invention. Various degradable and nondegradable polymeric matrices for use in controlled drug delivery are known in the art (Langer, R., Accounts Chem. Res. 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., Pharm. Res. 9:425-434 (1992); and Pec, et al., J. Parent. Sci. Tech. 44(2):58-65 (1990)). Alternatively, hydroxyapatite has been used as a microcarrier for controlled release of proteins (Ijntema, et al., Int. J. Pharm. 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Additionally, the disclosure provides methods for treating a neuroinflammatory disorder and/or neurodegenerative disorder by administering antibodies that bind to AD brain tissue. In one embodiment, the disclosure provides methods of treating a neuroinflammatory disorder and/or neurodegenerative disorder in a subject, comprising administering to the subject an anti-connective tissue growth factor (CTGF) antibody or antigen binding fragment thereof, thereby treating the neuroinflammatory disorder and/or neurodegenerative disorder in the subject.

Connective tissue growth factor (CTGF) is a matricellular protein of the CCN family of extracellular matrix-associated heparin-binding proteins. CTGF has important roles in many biological processes, including cell adhesion, migration, proliferation, angiogenesis, skeletal development, and tissue wound repair, and is critically involved in fibrotic disease and several forms of cancers.

"Antibody," as used herein, refers to an immunoglobulin or a part thereof, and encompasses any polypeptide comprising an antigen-binding site regardless of the source, species of origin, method of production, and characteristics. For the purposes of the present invention, it also includes, unless otherwise stated, antibody fragments such as Fab, F(ab')$_2$, Fv, scFv, Fd, dAb, diabodies, and other antibody fragments that retain antigen-binding function. Antibodies can be made, for example, via traditional hybridoma techniques, recombinant DNA methods, or phage display techniques using antibody libraries. For various other antibody production techniques, see Antibodies: A Laboratory Manual, eds. Harlow et al., Cold Spring Harbor Laboratory, 1988. The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity. The anti-CTGF antibodies disclosed herein are merely illustrative and any antibody that binds to CTGF or antigenic fragments thereof could be used.

The term "antigen-binding domain" refers to the part of an antibody molecule that comprises the area specifically binding to or complementary to a part or all of an antigen. Where an antigen is large, an antibody may only bind to a particular part of the antigen. The "epitope" or "antigenic determinant" is a portion of an antigen molecule that is responsible for interactions with the antigen-binding domain of an antibody. An antigen-binding domain may be provided by one or more antibody variable domains (e.g., a so-called Fd antibody fragment consisting of a VH domain). An antigen-binding domain may comprise an antibody light chain variable region (VL) and an antibody heavy chain variable region (VH).

"Antibody fragments" of "antigen binding fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al. Protein Eng. 8(10):1057-1062 [1995]); single-chain antibody molecules; and multispecific antibodies formed from antibody fragments.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework region (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FRs and, with the CDRs from the other chain, contribute to the formation of the antigen-binding site of antibodies (see Kabat et al., NIH Publ. No. 91-3242, Vol. I, pages 647-669 [1991]). The constant domains are not involved directly in binding an antibody to an antigen, but exhibit various effector functions, such as participation of the antibody in antibody dependent cellular cytotoxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (Θ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin. For further details, see Jones et al., Nature, 321:522-525 (1986); Reichmann et al., Nature, 332:323-329 (1988); and Presta, Curr. Op. Struct. Biol., 2:593-596 (1992). The humanized antibody includes a PRIMATIZED™ antibody wherein the antigen-binding region of the antibody is derived from an antibody produced by immunizing macaque monkeys with the antigen of interest.

A neuroinflammatory disorder is broadly defined as is inflammation of the nervous tissue. Neuroinflammation is widely regarded as chronic, as opposed to acute, inflammation of the central nervous system. Chronic inflammation is the sustained activation of glial cells and recruitment of other immune cells into the brain. It is chronic inflammation that is typically associated with neurodegenerative diseases. A neurodegenerative disorder is broadly defines as the progressive loss of structure or function of neurons, including death of neurons.

Examples of neuroinflammatory disorders and/or neurodegenerative disorders include Alzheimer's disease, Parkinson's disease, multiple sclerosis, amyotrophic lateral sclerosis (ALS), myasthenia gravis, chronic demyelinating polyneuropathy, Charcot Marie Tooth syndrome, neuromyelitis optica, optic neuritis, diffuse cerebral sclerosis, Shilder's encephalitis periaxialis diffusa, Huntington's Disease, Balo's concentric sclerosis, progressive supranuclear palsy, transverse myelitis, acute disseminated encephalomyelitis, necrotizing hemorrhagic encephalitis, leukodystrophies, CNS injury, stroke, age-related dementia, depression, bipolar disorder, Guillain-Bane syndrome, dementia, frontotemporal dementia, vascular dementia and chronic inflammatory demyelinating polyneuropathy (CIDP).

In one embodiment, the neuroinflammatory disorder and/or neurodegenerative disorder is Alzheimer's disease and the subject is human.

The antibodies disclosed in the present invention may be administered by intravenous, oral, intramuscular, subcutaneous or intrathecal administration.

The antibodies disclosed in the present invention may be used to treat early or mild stage Alzheimer's disease; middle or moderate stage Alzheimer's disease; or late or severe stage Alzheimer's disease. A subject with early or mild stage Alzheimer's disease may feel as if he or she is having memory lapses, such as forgetting familiar words or the location of everyday objects and may exhibit symptoms such as problems coming up with the right word or name; trouble remembering names when introduced to new people; challenges performing tasks in social or work settings; forgetting material that one has just read; losing or misplacing a valuable object and increasing trouble with planning or organizing.

A subject with middle or moderate stage Alzheimer's disease may confuse words, get frustrated or angry, or act in unexpected ways and may exhibit symptoms such as forgetfulness of events or about one's own personal history, feeling moody or withdrawn; especially in socially or mentally challenging situations; being unable to recall their own address or telephone number or the high school or college from which they graduated; confusion about where they are or what day it is; the need for help choosing proper clothing for the season or the occasion' trouble controlling bladder and bowels in some individuals' changes in sleep patterns, such as sleeping during the day and becoming restless at night' an increased risk of wandering and becoming lost and personality and behavioral changes, including suspiciousness and delusions or compulsive, repetitive behavior like hand-wringing or tissue shredding.

A subject with late or severe stage Alzheimer's disease may lose the ability to respond to their environment, to carry on a conversation and, eventually, to control movement and may exhibit symptoms such as needing round-the-clock assistance with daily activities and personal care; losing awareness of recent experiences as well as of their surroundings; experiencing changes in physical abilities, including the ability to walk, sit and, eventually, swallow; have increasing difficulty communicating and become vulnerable to infections, especially pneumonia.

The methods disclosed in the present invention may include the administration of additional therapeutic agents. Such therapeutic agents include donepezil, rivastigmine, galantamine, memantine or a combination thereof.

The antibodies or antigen binding fragments disclosed in the present invention may be conjugated to a toxic agent. Toxic agents are known in the art and may be used in the methods and compositions of the invention. For example, in some aspects, the therapeutic agent is a cytotoxic agent, a cytokine, an anti-angiogenic agent, a chemotherapeutic agent, a pro-apoptosis agent, an enzyme, a hormone, a growth factor, a peptide, a protein, an antibiotic, an antibody, a Fab fragment of an antibody, an antigen, a survival factor, an anti-apoptotic agent, a hormone antagonist, a virus, a bacteriophage, a bacterium, a liposome, a cell, a nucleic acid or an expression vector. Preferably, the agent is a cytotoxic agent, which may comprise a peptide, a polypeptide, or a small molecule, such as gelonin, ricin, abrin, diphtheria toxin, *Pseudomonas* exotoxin, *Clostridium perfringens* enterotoxin, dodecandrin, tricosanthin, tricokirin, bryodin, mirabilis antiviral protein, barley ribosome-inactivating protein (BRIP), pokeweed antiviral protein (PAPs), saporin, luffin, momordin, colicin, anthrax toxin, tetanus toxin, botulinum neurotoxin, and fragments thereof. For example, the cytotoxic agent comprises diphtheria toxin, the translocation enhancer region of diphtheria toxin, or the amino terminal 390 amino acids of diphtheria toxin. In another aspect, the cytotoxic agent may comprise *Pseudomonas* exotoxin KDEL (SEQ ID NO:05) or *Pseudomonas* exotoxin KDEL7 mutant (7mut).

The skilled artisan will understand that the agent may be an anti-angiogenic agent which includes, but not is not limited to, thrombospondin, angiostatin, endostatin or pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, paclitaxel, accutin, cidofovir, vincristine, bleomycin, AGM-1470, platelet factor 4 or minocycline. In a further aspect, the agent maybe a cytokine such as interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor).

For therapeutic purpose, the conjugate may be further defined as being comprised in a pharmaceutically acceptable carrier. There may also be provided a pharmaceutical composition comprising the conjugate for its superior therapeutic activity, a nucleic acid molecule comprising a sequence encoding the fusion protein defining the conjugate and an expression vector comprising the nucleic acid for various purposes.

The toxic agent may be conjugated to the antibody or antigen binding fragment by methods previously described or by any method known in the art. Examples of such toxic agents include cytotoxic agent, a cytokine, an anti-angiogenic agent, a chemotherapeutic agent, a pro-apoptosis agent, an enzyme, a hormone, a growth factor, a peptide, a protein, an antibiotic, an antibody, a Fab fragment of an antibody, an antigen, a survival factor, an anti-apoptotic agent, a hormone antagonist, a virus, a bacteriophage, a bacterium, a liposome, a cell, a nucleic acid or an expression vector.

In certain embodiments, the disclosed antibodies or antigen binding fragments of the present invention may be attached to imaging agents of use for imaging and diagnosis of various diseased organs, tissues or cell types. Many appropriate imaging agents are known in the art, as are methods for their attachment to proteins or peptides (see, e.g., U.S. Pat. Nos. 5,021,236 and 4,472,509, both incorporated herein by reference). Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label. Certain attachment methods involve the use of a metal chelate complex employing, for example, an organic chelating agent such a DTPA attached to the protein or peptide (U.S. Pat. No. 4,472,509). Antibodies or antigen binding fragments also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled antibodies or antigen binding fragments of the present invention may be produced according to well-known methods in the art. For instance, they can be iodinated by contact with sodium or potassium iodide and a chemical oxidizing agent such as sodium hypo chlorite, or an enzymatic oxidizing agent, such as lactoperoxidase. antibodies or antigen binding fragments according to the invention may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA). Also contemplated for use are fluorescent labels, including rhodamine, fluorescein isothiocyanate and renographin.

In certain embodiments, the disclosed antibodies or antigen binding fragments may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

In an additional embodiment of the invention, the antibodies or antigen binding fragments of the present invention may be conjugated to an agent which may improve antibody's ability to cross the BBB. The agent which facilitates or improves antibody's ability to cross the BBB may be conjugated to the antibody directly or through a linker comprising or consisting of a hydrazine linker, a disulfite linker, a thioether linker, a peptide linker, or the like. The agent which facilitates or improves antibody's ability to cross the BBB may comprise or consists of transferrin, insulin receptor bispecific antibodies or other targeting signals.

The present disclosure also provides methods of imaging brain tissue using the disclosed antibodies. In one embodiment, the invention provides methods of imaging brain tissue of a subject comprising contacting the brain tissue with an anti-CTGF antibody or antigen binding fragment thereof; and generating an image of the brain tissue.

In one embodiment the imaging is PET or MRI imaging.

In one embodiment, the invention provides methods of treating a neuroinflammatory disorder and/or neurodegenerative disorder comprising contacting brain tissue with an anti-CTGF antibody or antigen binding fragment thereof in a subject in need thereof.

In an embodiment, the brain tissue is in the hippocampus and the subject is human.

In another embodiment, the neuroinflammatory disorder and/or neurodegenerative disorder is Alzheimer's disease, Parkinson's disease, multiple sclerosis, amyotrophic lateral sclerosis (ALS), myasthenia gravis, chronic demyelinating polyneuropathy, Charcot Marie Tooth syndrome, neuromyelitis optica, optic neuritis, diffuse cerebral sclerosis, Shilder's encephalitis periaxialis diffusa, Huntington's Disease, Balo's concentric sclerosis, progressive supranuclear palsy, transverse myelitis, acute disseminated encephalomyelitis, necrotizing hemorrhagic encephalitis, leukodystrophies, CNS injury, stroke, age-related dementia, depression, bipolar disorder, Guillain-Bane syndrome, dementia, frontotemporal dementia, vascular dementia or chronic inflammatory demyelinating polyneuropathy (CIDP). In a specific embodiment, the neuroinflammatory disorder and/or neurodegenerative disorder is Alzheimer's disease.

In an additional embodiment, an additional therapeutic agent is administered and the additional therapeutic agent is donepezil, rivastigmine, galantamine, memantine or a combination thereof or any of the peptides previously described.

In further embodiments, the antibody or antigen binding fragment is conjugated to a toxic agent and/or is detectably labeled.

The disclosure further provides a method for detecting AD, or progression of AD in a subject. using the antibodies disclosed here. In one embodiment, the present invention provides a method of diagnosing, prognosing, or determining progression of a neuroinflammatory disorder and/or neurodegenerative disorder in a subject, or predicting benefit from therapy in a subject having a neuroinflammatory disorder and/or neurodegenerative disorder in a subject, comprising contacting brain tissue in the subject with an anti-CTGF antibody or antigen binding fragment; and diagnosing, prognosing, or determining progression of the neuroinflammatory disorder and/or neurodegenerative disorder or predicting benefit from therapy in the subject.

In certain embodiments the brain tissue is the hippocampus and the neuroinflammatory disorder and/or neurodegenerative disorder is Alzheimer's disease. In another embodiment, the subject is human. In some embodiments, an additional therapeutic agent, such as donepezil, rivastigmine, galantamine, memantine or a combination thereof is administered.

In another embodiment, the brain tissue is imaged by PET or Mill imaging.

Positron-emission tomography (PET) is a nuclear medicine functional imaging technique that is used to observe metabolic processes in the body. The system detects pairs of gamma rays emitted indirectly by a positron-emitting radionuclide (tracer), which is introduced into the body on a biologically active molecule. Three-dimensional images of tracer concentration within the body are then constructed by computer analysis. In modern PET-CT scanners, three-dimensional imaging is often accomplished with the aid of a CT X-ray scan performed on the patient during the same session, in the same machine.

Synaptic activity can be determined by brain fludeoxyglucose (FDG) PET. FDG is a glucose analog and is suitable for indicating brain metabolism when labeled with Fluorine-18 for PET imaging. Studies using FDG PET have identified an AD signature including posterior midline cortices of parietal and posterior cingulate gyri, the inferior parietal lobe, posteriolateral portions of the temporal lobe as well as the hippocampus and medial temporal cortices. FDG PET has emerged as a marker of neurodegeneration with which hypometabolism can be observed to precede the appearance of cognitive symptoms and to predict the rate of decline in individuals with AD. Additionally, techniques have been developed for amyloid PET in AD using amyloid tracers such as $^{18}$F florbetaben, $^{18}$F florbetapir, and $^{18}$F flutemetamol. These techniques allow for clinical determination of amyloid content in the brain.

Magnetic resonance imaging (MRI) is an imaging technique used in radiology to form pictures of the anatomy and the physiological processes of the body in both health and disease. MM scanners use strong magnetic fields, radio waves, and field gradients to generate images of the organs in the body. MRI is often divided into structural MRI and functional MRI (fMRI). fMRI can be regarded as the method providing dynamic physiological information, whereas structural imaging provides static anatomical information. In AD, structural MRI can be used to assess progressive cerebral atrophy and changes in tissue characteristics which cause signal alterations. Structural MRI can be used to measure progression of AD. fMRI can be used to probe the functional integrity of brain networks supporting memory and other cognitive domains.

In an additional embodiment, the antibody or antigen binding fragment is conjugated to a toxic agent and/or is detectably labeled.

In a further embodiment, prognosing or determining progression of Alzheimer's disease comprises determining the expression level of glial fibrillary acidic protein (GFAP) in the hippocampus. The determining the expression level of GFAP may comprise imaging the brain tissue.

The disclosure further provides compositions to treat, diagnose, prognose or determine progression of a neuroinflammatory disorder and/or neurodegenerative disorder comprising a small molecule compound, an oligonucleotide or an aptamer. In one embodiment, the composition comprises a pharmaceutically acceptable salt.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLE 1

Peptides Recognizing Changes in Alzheimer's Disease Brain

A new approach was taken to AD, searching for previously unknown markers for the disease by using phage library screening. An in vivo phage library screening was developed to probe molecular specificities in the vasculature. This approach has been successfully utilized to probe the in situ environment of tumors and some other pathologies. In vivo phage peptide library screens were conducted to probe for signatures in AD brain. Given that AD includes a vascular component, it is likely that the vasculature in AD expresses specific markers.

The screens discussed herein employed a transgenic rodent model of AD. The characteristics desired in the peptides were specificity for AD versus normal brain (and ultimately with regard to brain diseases other than AD), recognition of AD at the earliest stages of the disease, abundance of peptide accumulation in the brain, and ability to recognize human AD. An additional desirable characteristic was recognition of an AD marker on endothelial cells because of the availability of the blood vessels to circulating probes regardless of the status of the blood-brain barrier (BBB).

Through this approach, the inventors have identified a panel of targeting peptides that can recognize AD brains at different stages of the disease, starting from early to advanced stage.

Results

In vivo phage screening was conducted using a T7 phage library expressing random peptides with the composition of $CX_nC$ (C=cysteine; X=any amino acid; n=7). The mouse model used for this screening is the hAPP-J20 that expresses amyloid precursor protein (APP) with both the Swedish and Indiana mutations (Murrell et al., Science 254, 97-99. (1991); Mullan et al., Nat. Genet. 1, 345-347. (1992)). Peptides homing to the hippocampus of these mice was the focus because the hippocampal region is where the AB-related lesions and damage are most prevalent early on in the disease.

A $CX_7C$ phage library was intravenously injected into 9 month-old AD and wild-type (WT) littermate mice, and allowed to circulate for 30 min, after which mice were perfused with saline, brains were collected, and the hippocampal region was dissected and subjected to phage titration and high throughput sequencing of the phage inserts. A surprise result was that the number of phage recovered from the AD hippocampus samples was much higher than the number recovered from a similar screen on normal littermates of the AD mice (FIG. 1A). This result was attributed to a breakdown of the BBB in the AD mice, which allows phage to enter the space normally across the BBB. BBB leakage has also been reported in AD patients.

Parallel phage library screens were performed on a normal mouse and a 9-month old AD transgenic mouse (J20 hAPP tg mouse line, which expresses transgenic amyloid precursor protein with two disease-related mutations). The library was intravenously injected into anesthetized mice and the hippocampal area of the brain was collected 30 min after intravenous injection of the library, phage was isolated from the tissue samples and subjected to high throughput sequencing of the peptide-encoding inserts in the phage DNA. Table 1 list most abundantly represented peptide from the two kinds of brains, and all peptides with significant representation in the AD brain and absent or nearly absent in the normal brain are listed in Table 2. Two peptides, CASPRLSKC (SEQ ID NO: 3) and CESPLLSEC (SEQ ID NO: 11), from among the highest scoring ones were subjected to detailed studies as described below.

TABLE 1

The most represented peptides from phage screens with normal and AD mice.

| Peptide (SEQ ID) | Frequency/% |
|---|---|
| Wild-type mouse | |
| 84 | 4.677875622 |
| 85 | 3.558881234 |
| 86 | 2.377150157 |
| 87 | 2.372587489 |
| 88 | 2.285896792 |
| 89 | 1.845599306 |
| 90 | 1.737235936 |
| 91 | 1.669936579 |
| 92 | 1.495414518 |
| 93 | 1.425833828 |
| 94 | 1.244467765 |
| 95 | 1.171465073 |
| 96 | 1.098462381 |
| 97 | 1.089337044 |
| 98 | 1.022037688 |
| 99 | 0.97070767 |
| Alzheimer's mouse | |
| 2 | 0.854936569 |
| 3 | 0.722559294 |
| 4 | 0.395555906 |
| 5 | 0.388464266 |
| 6 | 0.376644866 |
| 100 | 0.334882988 |
| 7 | 0.334095028 |
| 9 | 0.322275628 |
| 10 | 0.319123789 |
| 11 | 0.315971949 |

TABLE 2

Peptides homing preferentially to AD brain.

| Peptide | SEQ ID NO |
|---|---|
| CSKTTE | 2 |
| CASPRLSKC | 3 |
| CEQVRQKRC | 4 |
| CNSKETSRC | 5 |
| CSPE | 6 |
| CLTDNEETC | 7 |
| CQGPRPVKC | 8 |
| SSVDKL | 9 |
| CTKTAK | 10 |
| CESPLLSEC | 11 |
| CES | 12 |
| CGDTKIGKC | 13 |
| CDPSDTNVC | 14 |
| CRPVIKANC | 15 |
| CGKKSTEGC | 16 |
| CRTVKR | 17 |
| CRQGNKKQC | 18 |
| CATEQVVEC | 19 |
| CQYNKTNGAKL | 20 |
| CRVQKSGLAKL | 21 |
| AGGLDDSVLSL | 22 |
| CASPC | 23 |
| CTSMRKPGC | 24 |
| CGADEEIC | 25 |
| CSRSND | 26 |
| CEEQLYSGAKL | 27 |
| CTGGKSSSC | 28 |
| CRRKTS | 29 |
| CAQLAEAR | 30 |
| CQNSRRSNC | 31 |
| CDTVSK | 32 |
| CAEGRRVSAKL | 33 |
| CDPSDTNVLLSL | 34 |
| CDRTQRTAKL | 35 |
| CEDE | 36 |
| SCRKTPEKKC | 37 |
| CKGSGLKTC | 38 |
| CSVGRTVKC | 39 |
| CAKLAKGC | 40 |
| CAKLRAAAC | 41 |
| CLSTKTKTC | 42 |
| CLQK | 43 |
| CKPAPNQKC | 44 |
| CTVKLSRTC | 45 |
| CGIEVREDC | 46 |
| CKNGGTAVC | 47 |
| CAHPARTKC | 48 |
| CGLGRVTKC | 49 |
| CAGD | 50 |

TABLE 2-continued

Peptides homing preferentially to AD brain.

| Peptide | SEQ ID NO |
|---|---|
| CPQNQRVKC | 51 |
| CSKLSR | 52 |
| SCEDTVRVGC | 53 |
| CADGRL | 54 |
| CARPDKEEC | 55 |
| CERLTSAGC | 56 |
| CSKSV | 57 |
| CHSNHESDC | 58 |
| CDRKDDIVC | 59 |
| CNGEGKRGC | 60 |
| CPRVLK | 61 |
| CDARLKRGC | 62 |
| CALRDGDIC | 63 |
| CRGPSDKGC | 64 |
| CNKAPTTRC | 65 |
| CGDRKGPRC | 66 |
| CLAMVEADC | 67 |
| CHVRTDDPC | 68 |
| CARESNKKC | 69 |
| CSSRRSTGC | 70 |
| CKAGDDNSC | 71 |
| CRKRDSGRC | 72 |
| CKPLANDNC | 73 |
| CLGRREKDC | 74 |
| CHRDAKGGC | 75 |
| CTAQSPPAC | 76 |
| CRRPMAQC | 77 |
| CGMKGDTC | 78 |
| AGGLG | 79 |
| CKANRDTKC | 80 |
| CRTSPDRGC | 81 |
| CMSEGSV | 82 |
| CSRARSE | 83 |
| CVPKGKLVC | 84 |
| CKVRKSEGC | 85 |
| CVPKGKLVLLSL | 86 |
| CATPRDKRTC | 87 |
| CLSLD | 88 |

TABLE 2-continued

Peptides homing preferentially to AD brain.

| Peptide | SEQ ID NO |
|---|---|
| CSGDMETKC | 89 |
| CSDRRLIDC | 90 |
| CARVKK | 91 |
| CRKQPTNVC | 92 |
| CSTNA | 93 |
| CADDGC | 94 |
| CRTPLNPRC | 95 |
| CTREGNETC | 96 |
| CELSQ | 97 |
| CSRTSKQAC | 98 |
| CTVNGKRSC | 99 |
| CSGKAQRGC | 100 |

Figure 2:
FIG. 2 is a pictorial representation depicting a consensus peptide motif from screens at different stages of AD (SEQ ID NOs: 105-131 from top to bottom). Phage library screening was performed on J20 AD mice at different ages. The insert sequences were analyzed using a motif search program.

A series of screens on AD mice at the ages of 3, 5, 7, and 9 months showed that the increased yield of phage from the AD hippocampus was already present at 3 months of age. The screen yielded a shared peptide motif represented in each of the age groups (FIG. 2). The motif sequence is $X_1X_2X_3X_4$, wherein $X_1$ is G or A; $X_2$ is K, R, or H; $X_3$ is K, R, or H; and $X_4$ is N or Q (SEQ ID NO: 101).

A consensus peptide with this motif (CDAGRKQKC; SEQ ID NO: 102) was named DAG. CDAGRKQKC (SEQ ID NO: 102; referred to herein as "DAG").

Figure 1B:
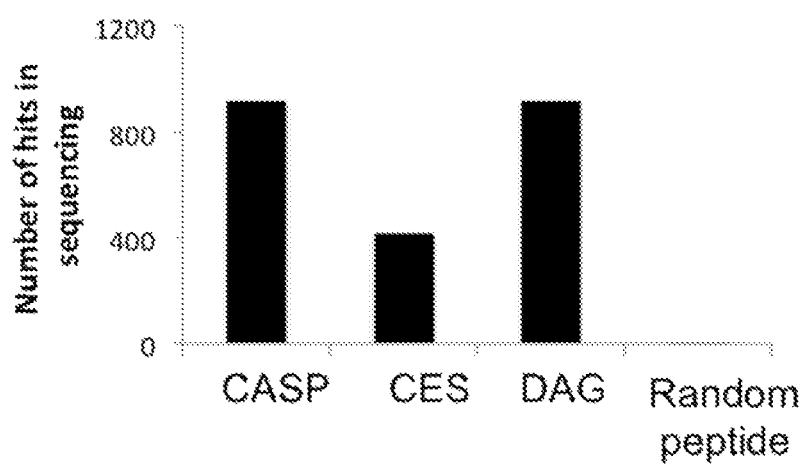

FIG. 1B shows that intravenously injected phages displaying SEQ ID NO: 3, SEQ ID NO: 11 or DAG (SEQ ID NO: 102), all home to AD hippocampus with high specificity. These phages showed no accumulation in normal brain (results not shown).

The inventors have synthesized each of the three peptides and confirmed their AD specificity as fluorescein-amide (FAM)-labeled peptides in-vivo homing in AD animals and by binding of nanoparticle conjugates on tissue sections (data not shown). FAM-CESPLLSEC and FAM-CASPRLSKC both homed to AD, but not normal, hippocampus from an intravenous injection. CASPRLSKC, CESPLLSEC and DAG peptides homed to the dentate gyms of AD brain but not normal brain. The synthetic peptides were labeled with FAM and 100 nmol and were intravenously injected to 9-month old AD mice through the tail vein. The peptides were allowed to circulate for 30 min, after which the mice were perfused with 20 ml of PBS, the brains were collected and snap-frozen in OCT for sectioning. The peptides were detected by anti-FAM staining (green), nuclei were stained with DAPI (blue), and anti-CD31 was used to visualize blood vessels.

The inventors also conjugated CASPRLSKC onto silver nanoparticles and showed that they specifically bind to AD brain sections (data not shown). CASPRLSKC recognizes the AD hippocampus in tissue section overlay assay. Silver nanoparticles were coated with the CASPRLSKC peptide or a control peptide and used to overlay brain sections from AD and normal mice. Silver staining was used to visualize binding and nuclei were stained with nuclear fast red. The CASPRLSKC nanoparticles bind to elongated structures that may represent nerve fibers. These structures are not present in the normal brain. The control nanoparticles showed no binding to AD or normal brain.

The characterization of the DAG peptide is farthest along of the three peptides. DAG peptide targets AD hippocampus and co-localizes with astrocytes. Intravenously injected FAM-DAG specifically homed AD hippocampus (data not shown). Further analysis indicated that the target cell type for DAG peptide is a reactive astrocyte in the neurovascular unit and in the hippocampus in the AD brain (data not shown). In AD, astrocytes are known to become reactive, particularly around amyloid plaques.

Figure 3:
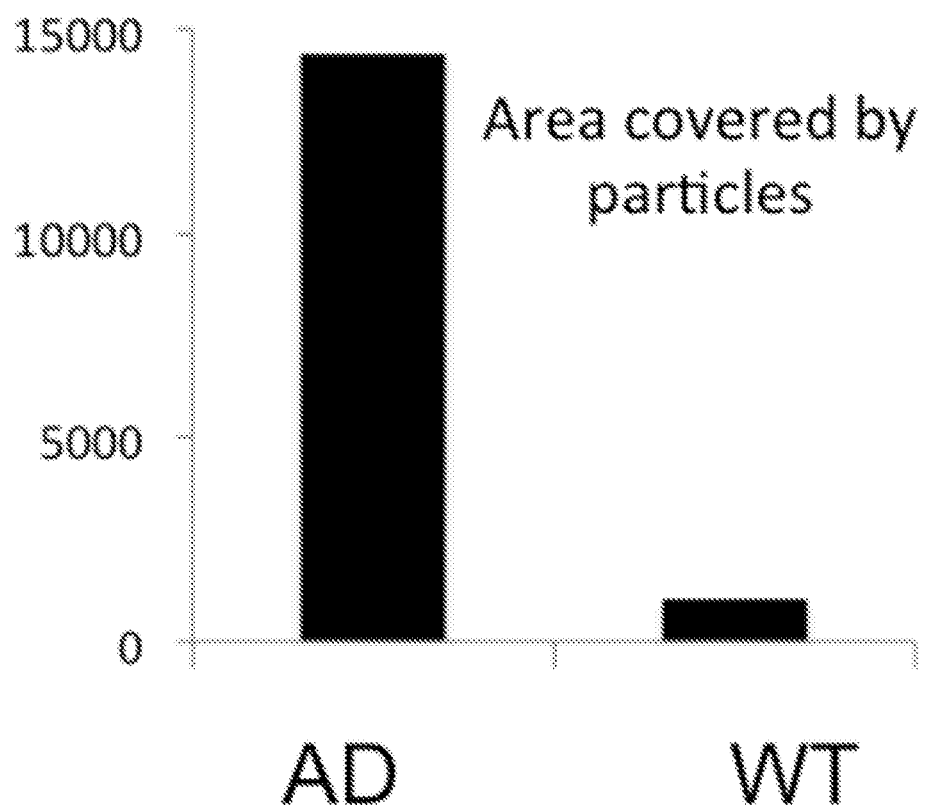
FIG. 3 is a graphical representation of data pertaining to DAG-coated silver nanoparticles (DAG-AgNPs) binding to the AD hippocampus in brain sections. DAG AgNPs showed 14-fold higher binding to the hippocampal CA1 region in AD brains than in WT brains.

Binding of DAG conjugated silver nanoparticles on frozen brain sections from AD or WT animals in overlay binding assay was also tested. Data suggested that DAG conjugated nanoparticles bind over 10 fold higher to sections from the AD brain as compared to sections from an age-matched normal wild-type brain (FIG. 3). This binding is restricted to the hippocampal region CA1 and the dentate gyrus. Frozen coronal sections from AD and WT mice were used for overlay experiments with DAG-AgNPs. Silver staining was used to visualize binding and nuclei were stained with nuclear fast red. DAG AgNPs showed 14-fold higher binding to the hippocampal CA1 region in AD brains than in WT brains as shown in FIG. 3.

Figure 4:
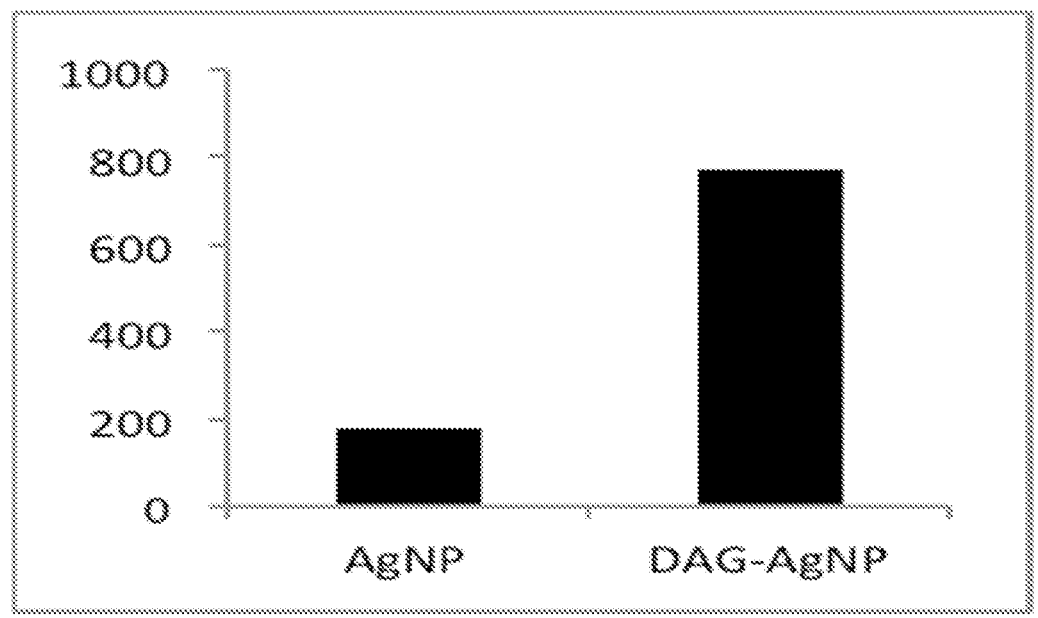
FIG. 4 is a graphical representation of data pertaining to DAG-coated silver nanoparticles (DAG-AgNPs) binding to human IPS cell-derived endothelial cells (ECs) from an AD patient, but not to ECs derived from a normal donor. The bar diagram shows quantification of the DAG-AgNP vs. control AgNP binding to the AD ECs.

The mouse AD models only go so far in mimicking the human disease, so it is important to test the peptides for their ability to recognize human AD samples. The inventors have thus far shown that DAG recognizes endothelial cells differentiated from AD iPS cells and not cells prepared similarly from a control individual (FIG. 4). The inventors have also shown using nanoparticles coated with this peptide in overlay of brain sections that DAG peptide coated nanoparticles bind to sections from an AD patient with sporadic AD, but control particles do not (not shown).

DAG-AgNPs bind to human iPS cell-derived endothelial cells (ECs) from an AD patient, but not to ECs derived from a normal donor (FIG. 4). Human iPS cell-derived from an AD patient and from a normal individual were differentiated into endothelial cells and the cultured cells were used in an overlay assay with DAG-coated and control AgNP. The bar diagram of FIG. 4 shows quantification of the DAG-AgNP vs. control AgNP binding to the AD ECs.

These results indicate that in vivo phage screening on AD mice can yield homing peptides specific for AD brain. These peptides provide probes for targeted delivery of therapeurics and diagnostics into the parts of the brain affected by the disease. The target molecules for the peptides, once identified, will provide new information on the pathogenesis of AD and are potentially druggable targets.

EXAMPLE 2

In Vivo Phage Display in Alzheimer's Disease Reveals a Novel Peptide for Targeting Neuroinflammation The inventors set out to search for AD-specific molecular markers in the neurovascular unit of the brain. In vivo phage display of a random peptide library in the hAPP-J20 transgenic mouse model of AD at four different ages revealed phages displaying the cyclic peptide, DAG (SEQ ID NO: 102) that accumulated in the hippocampus of the hAPP-J20 mice. The DAG peptide homed after systemic injection to endothelial cells and astrocytes in the hippocampus of both hAPP-J20 and Tg2576 mouse models of AD. Extravascular astrocytes also took up the peptide. The target for DAG in the brain was identified as connective tissue growth factor (CTGF), a matricellular protein known to be highly expressed in mouse and human AD. DAG targeted early stages of AD, preceding amyloid deposition, localizing both in the hippocampus and cortex of hAPP-J20 mice. DAG also homed to cells in human glioblastoma, traumatic brain injury, and Parkinson's disease brain, all of which express elevated levels of CTGF. DAG thus provides a tool for targeted delivery of therapeutics and imaging agents into neuroinflammatory lesions, and the findings also have implications for pathogenesis of AD and additional neurodegenerative disorders with a neuroinflammatory component.

Materials and Methods

Animal Models

All animal experiments were conducted under an approved protocol of the Institutional Animal Care and Use Committee of Sanford Burnham Prebys Medical Discovery Institute. The following transgenic mouse models were used for peptide homing studies—hAPP-J20 (Ruoslahti, Nature genetics 1, 345-347 (1992)), Tg2576 (Jacobsen et al., Proc Natl Acad Sci USA 103, 5161-5166 (2006)), and mTHY-1-α-synuclein model (Chesselet et al., Neurotherapeutics 9, 297-314 (2012)). The P13 glioblastoma model is a patient-derived orthotopic xenograft model (Bougnaud et al., Oncotarget, (2016)). Spheroids were cultured as described previously (Bjerkvig et al., J Neurosurg 72, 463-475 (1990)). After two weeks in culture, spheroids (volume 2.5 µl) were stereotactically implanted into the brains of nude mice. Mice were used approximately 6 weeks after tumors were induced, when mice started presenting neurological symptoms. The acute brain injury model was setup as previously described (Mann et al., Nature communications 7, 11980 (2016)). Briefly, 8 to 10 week-old male BL6 mice were anaesthetized with 4% isoflurane in 70% $N_2O$ and 30% $O_2$, and a 5-mm craniotomy was performed using a portable drill and a trephine over the right parietotemporal cortex using a stereotactic frame. The bone flap was removed and nine needle punctures using a 21G needle were made 3 mm deep according to a 3×3 grid, spaced 1 mm in width and 1 mm in height. The scalp was then closed with sutures, anesthesia discontinued and mice were administered buprenorphine i.p. for pain control.

In Vivo Phage Display hAPP-J20 mice were intravenously injected with 1e10 pfu of a $CX_7C$ (wherein X is any amino acid) naïve phage library, in 100 µL of PBS. The library was allowed to circulate for 30 minutes, after which mice were anesthetized with 2.5% avertin and perfused with PBS intracardially. The brain was removed and the hippocampus was extracted and homogenized in LB-NP 40 (1%) and phage was processed as described (Teesalu et al., Methods Enzymol 503, 35-56 (2012)). The phages in the lysate were rescued by amplification in E. coli and peptide-encoding portion of the phage genome was sequenced using Ion Torrent high throughput sequencing.

Homing Studies and Tissue Sections

For peptide homing, mice were intravenously injected with 50 nmole peptide dissolved in PBS, and allowed to circulate for 30 min. Mice were then perfused intracardially with saline and all major organs were isolated and fixed in 4% paraformaldehyde (PFA) at pH 7.4 overnight. The organs were then washed with PBS and placed in graded sucrose solutions overnight before optimal cutting temperature compound (OCT) embedding. Ten-micro-meter-thick sections were cut and analyzed by immunostaining.

Peptide Synthesis and Coupling

The peptides were synthesized on a microwave-assisted automated peptide synthesizer (Liberty; CEM, Matthews, N.C.) following Fmoc/t-Bu (Fmoc:Fluorenyl methoxy carbonyl, t-Bu: tertiary-butyl) strategy on rink amide resin with HBTU (N,N,N',N'-Tetramethyl-O-(1H-benzotriazol-1-yl) uranium hexafluorophosphate (OR) O-(Benzotriazol-1-yl)-N,N,N',N'-tetramethyluronium hexafluorophosphate) activator, collidine activator base and 5% piperazine for deprotection. Fluorescein and biotin tags were incorporated during synthesis at the N-terminus of the sequence. Cleavage using a 95% TFA Trifluoro acetic acid followed by purification gave peptides with >90% purity. Peptides were lyophilized and stored at −20° C.

ELISA

Human CTGF recombinant protein (Affymetrix Cat #14-8503-80) was incubated on Nunc low-binding plates at concentration of 10 µg/ml for overnight at 4° C. Excess protein in the plates was removed by washing with PBS-T (PBS with 0.005% Tween 20). Plates were blocked with 200 µl of 3% non-fat milk in PBS for 1 hour at room temperature and washed with PBS-T once. Biotin-labeled peptide (at different concentrations) in PBS was added to the plate for 2 hours at 37° C. For peptide inhibition, non-labeled DAG peptide (0.5 mM) was added 30 minutes prior to addition of labeled peptide. The plates were washed with 100 µl PBS-T for three times to remove excess peptide. The bound peptide was detected by incubating with 100 µl of Vectastain ABC™ reagent (Vector labs, Burlingame, Calif.) for 30 minutes. The plate was washed with 100 µl PBS-T three times. Next, 100 µl of o-phenylenediamine dihydrochloride (OPD) silver and gold substrate (Sigma-Aldrich) was added to the wells and incubated at room temperature until visible color was observed (~30 min). Adding 50 µl of 1 M H$_2$SO$_4$ stopped the reaction and the plate was read at 495 nm (FlexStation™ 3 Reader, Molecular Devices, Sunnyvale, Calif., USA).

Tissue Section Overlays of FAM Labeled Peptides

PFA fixed sections were incubated in PBS for 10 minutes, followed by PBS-Triton-x-100 (0.2%) for 10 minutes. Sections were rinsed with PBST, mounted in a slide holder, and subsequently washed with PBS-T during 12 minutes. Slides were blocked with blocking buffer for 60 minutes at room temperature. Then, peptides were incubated at a concentration of 10 µg/mL dissolved in concentrated blocking buffer, for three hours at room temperature. Sections were then washed with three 4-minute washes of PBS-T, and subsequently fixed with PFA for 10 minutes, followed by three 3-minute washes with PBS-T. Sections were then incubated with primary antibody at 1/200 in diluted blocking buffer overnight at 4° C. Later, sections were washed with three 4-minute washes with PBS-T. Slides were then incubated with secondary antibody at 1/200 dilution in diluted blocking buffer for 30 minutes at room temperature, followed by three 4-minute washes of PBS-T. Sections were then counterstained with DAPI for 5 minutes, washed with PBS-T and mounted.

Immunofluorescence

Frozen sections were permeabilized using PBS- 0.2% Triton™ X-100 (PBST), blocking was carried out using blocking buffer (5% BSA, 1% goat serum, 1% donkey serum in PBST. Primary antibodies were incubated in diluted (1%) blocking buffer overnight at dilutions 1/100 or 1/200 at 4° C., washed with PBST and incubated with secondary antibodies diluted 1/200 or 1/500 in 1% diluted buffer for 1 hour at room temperature, subsequently washed with PBST, counterstained with DAPI 1 µg/mL in PBS for 5 minutes, washed with PBS, mounted using aqueous mounting media (Vector Biolabs), and imaged using a confocal microscope (Zeiss LSM-710). Staining was done using the following antibodies and reagents: anti-fluorescein (Invitrogen A889), CD31 (BD Biosciences clone MEC 13.3), aβ (Sigma clone 6E10), GFAP (Invitrogen clone 2.2B10), CTGF (Santa Cruz, clone C-19).

Affinity Chromatography and Proteomics

For identifying DAG binding proteins, the human glioblastoma astrocytoma cell line U251 was lysed in PBS containing 200 mM n-octyl-beta-D-glucopyranoside and protease inhibitor cocktail (Roche) as described previously with slight modifications. The clarified lysates were loaded on to Sera-Mag magnetic particles (GE Healthcare Lifesciences, USA) coated with biotin-DAG, and incubated overnight with rotation at 4° C. The magnetic beads were washed with wash buffer followed by additional washing with 0.5 mM control peptide (CRKQGEAKC; SEQ ID NO: 103) to remove non-specifically bound proteins. The bound proteins were eluted with 1 mM free DAG peptide. The eluted factions were pooled, their protein concentration determined by using bicinchoninic acid (BCA) protein assay (Pierce) and the samples were digested using the Filter-aided Sample Preparation (FASP) method. Finally, the digested samples were dried, desalted and subjected to LC-MS/MS analysis at the Sanford Burnham Prebys Medical Discovery Institute's Proteomics Core facility. All mass spectra were analyzed with MaxQuant™ software version 1.5.0.25. The MS/MS spectra were searched against the Uniprot™ protein sequence database (version July 2014).

Generation of Brain Microvascular Endothelial Cells from hiPSCs

The details of human induced pluripotent stem cells (hiPSCs) derived from Alzheimer disease patients with APP duplication, and non-demented control individuals, are described previously (Israel et al., Nature 482, 216-220 (2012)). These hiPSCs were extensively characterized and have been established as an excellent human model for AD. An additional AD hiPSC line generated from dermal fibroblasts from a 56-year-old individual harboring a Presenilin1 (PSEN1) mutation (Coriell Institute, Cat #AG06840) was used to further validate the results from the APP lines. hiPSCs were routinely maintained on mouse embryonic fibroblast as described before (Lin et al., Nat Methods 6, 805-808 (2009); Talantova et al., Proc Natl Acad Sci USA 110, E2518-2527 (2013)). Brain microvascular endothelial cells differentiation of hiPSCs was performed using a previously described protocol (Lippmann et al., Nature biotechnology 30, 783-791 (2012), with minor modifications. Briefly, feeder-free cultures of hiPSCs were allowed to spontaneously differentiate in the absence of bFGF for 5-7 days, and then transferred to Endothelial cell (EC) medium composed of human Endothelial Serum-Free Medium™ (Invitrogen) supplemented with 20 ng/ml bFGF and 1% platelet-poor plasma-derived bovine serum (PDS; Biomedical Technologies). After 1-2 days the cells were dissociated with dispase (2 mg/ml) and were plated on 12 well plates coated with a mixture of collagen IV (400 µg/ml) and fibronectin (100 µg/ml). Cells were then cultured in EC medium until they reached confluence, after which they were split and expanded to near 100% purity. BBB-type EC identity was confirmed by flow cytometry or double immunoreactivity to the hallmark efflux transporter p-glycoprotein and other EC markers (CD31, GLUT-1, PECAM, Occludin, and Claudin-5). Furthermore, the capability of these cells to make functional tight junctions and polarized efflux activity was validated using a dual chamber efflux transport assay as described before.

Silver Nanoparticles Synthesis

Silver nanoparticles (AgNPs) with PEG coating and peptide functionality were prepared as reported previously with some modifications (Braun et al., Nature materials 13, 904-911 (2014)). AgNPs of ~35 nm diameter were synthesized by citrate acid reduction of silver nitrate in solution. First, $AgNO_3$ (450 mg) dissolved in 2.5 L water was stirred and heated to a boil and 50 mL water containing trisodium citrate dihydrate (500 mg, Sigma) was added. After 30 min the solution was cooled to room temperature. The resulting optical density at 405 nm was ~10. To install the coating, lipoic PEG amine (LPN, 51.9 mg, 3400 g/mol, Nanocs) was dissolved and reduced for 3 h in 4.1 mL of aqueous 84 mM tris-carboxylethyl phosphine pH 7.0 (Sigma). AgNPs (500 mL) were heated to 50° C. and LPN solution (0.79 mL) was added, followed by 0.25 mL of 0.5 M TCEP. After 30 min incubation the solution was cooled to room temperature (RT) forming LPN-AgNPs. Tween 20 (T20, 0.25 mL, 10% in water) and 20 mL 2 M NaCl were sequentially added to the LPN-AgNPs and incubated overnight at 4° C. Using a stirred cell apparatus (Millipore) equipped with a 100 kDa membrane LPN-AgNPs were washed and concentrated 50-fold into 0.5× PBS with 0.005% T20 and 5 mM TCEP. LPN-AgNPs were further passivated by adding 0.03 mM N-acetyl-L-cysteine methyl ester (Sigma) for 2 h, followed by 0.10 mM tetracysteine peptide (acetyl-CCPGCC-amide, LifeTein) for 2 h. LPN-AgNPs were washed twice at 15k RCF and resuspended to 400 O.D. in 0.05 M phosphate buffer with 0.005% T20 pH 7.3. This product could be stored at least 6 months at 4° C. To attach peptide, a bifunctional linker was reacted with 1 mL of the LPN-AgNPs to introduce maleimide groups (10 mg, NHS-PEG-Mal, 2 kDa JenKem USA, 1 h at RT), then washed with 0.1 M HEPES buffer pH 7.2 0.005% T20 by centrifugation (4C, 11 kxg 15 min, three times), and immediately reacted for 1 h with freshly dissolved cysteine peptide (final concentration ~0.1 mM FAM-cys-x-DAG-$NH_2$) or a control thiol-containing peptide. X indicates aminohexanoic acid linker. The product peptide-AgNPs were washed with PBS 0.005% T20 (PBST), then filtered (0.22 μm). The Ag plasmon peak was 300 at 405 nm. The inventors estimated ~15 nM in AgNPs using an extinction coefficient of $2\times10^{10}$ $M^{-1}$ $cm^{-1}$ for spherical silver.

In Vitro Binding Experiments

Cell binding experiments on U251 cells and hiPSCs were with done using peptide conjugated AgNP. U251 cells were cultured in a 96-well plate. The cells were blocked with 200 μl of 10% FCS in HBSS (Hanks' Balanced Salt Solution from Gibco) for 30 min at 37° C. Following that, DAG-AgNPs (0.5 nM concentration diluted in HBSS) alone or in the presence of free non-labeled peptide (200 μM) were incubated on the cells for 1 hour at 37° C. After washing the unbound AgNP with HBSS three times, the plates were imaged with fluorescent microscopy by looking at intrinsic emission from the FAM tag on the peptide. hiPSCs were cultured in 48 well plate and similar protocol as described above was followed, with the exception that AgNP concentration for incubation was kept at 0.15 nM. Nanoparticle binding was quantified from fluorescence micrographs using ImageJ™ software.

Human Tissue Experiments

Postmortem human brain samples were obtained from the New York Brain Bank at Columbia University, New York. The patient was an 82-year-old male with a diagnosis of AD neuropathologic changes ([A3, B3, C3]). The normal brain tissue was obtained from BioChain Institute Inc. (Newark, Calif.). The donor was a 54 year-old male without any neurologic diagnosis on detailed neuropathologic evaluation. The Parkinson's disease brain tissue was obtained from UCSD Pathology bank. Frozen brain tissue was sectioned for immunohistochemistry and ex vivo overlay binding with FAM-peptides.

Statistical Analysis

All data represents mean value±SEM. All the significance analysis was done using Statistica™ 8.0 software, using one-way ANOVA or two-tailed heteroscedastic Student's t test. The details of the statistical tests carried out are indicated in respective figure legends.

Results

In Vivo Phage Screening in a Mouse AD Model

Figure 5A:
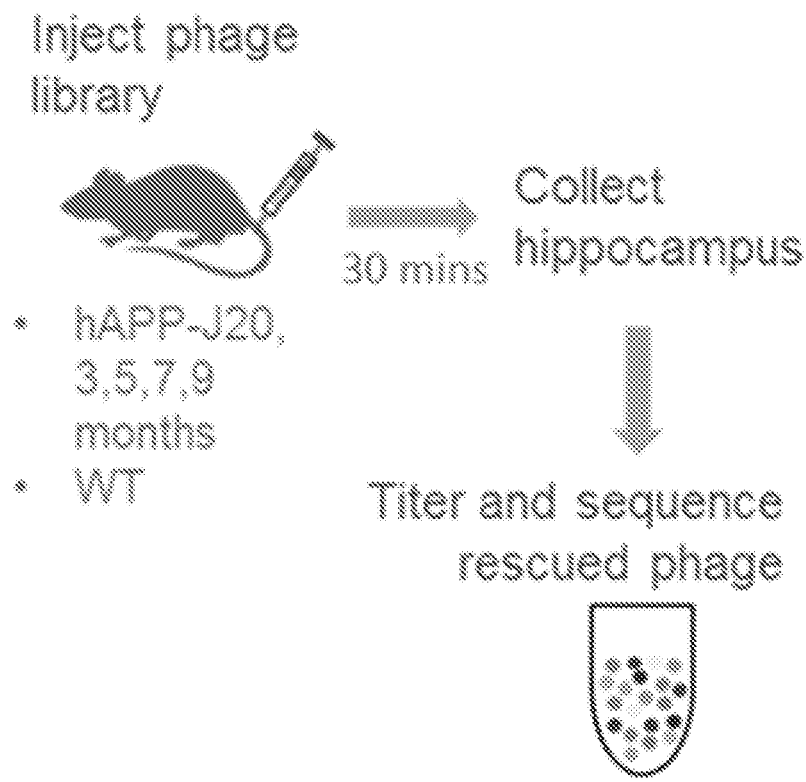
FIGS. 5A-5B is a series of pictorial and graphical representations relating to identification of DAG peptide by phage screening in transgenic mouse model of AD.
Figure 5B:
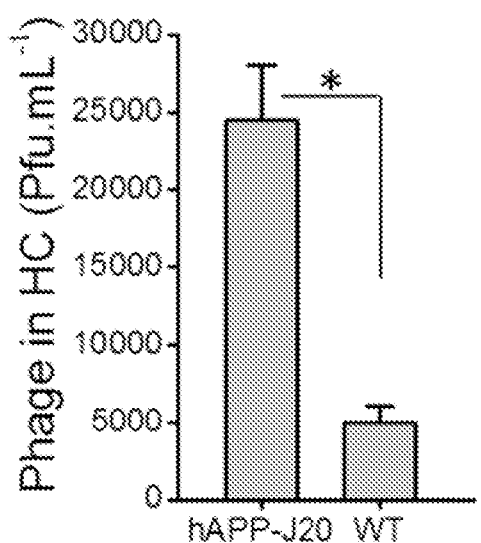

To identify peptides specific for AD brain, in vivo phage display was performed using a T7 phage library that displays 9-amino acid cyclic peptides with the general composition of $CX_7C$ (C=cysteine; X=any amino acid) on the phage surface. The library was injected intravenously into the hAPP-J20 transgenic mouse model of AD and their age-matched wild-type (WT) littermates in four different age groups (FIG. 5A). Four-fold higher phage titers were recovered from the hippocampi of 9-month-old hAPP-J20 than WT mice (FIG. 5B), whereas there was no significant difference in the younger age groups. These results suggest possible permeability of the BBB at 9 months of age, a time when the hAPP-J20 mice have fully developed disease.

Figure 6:
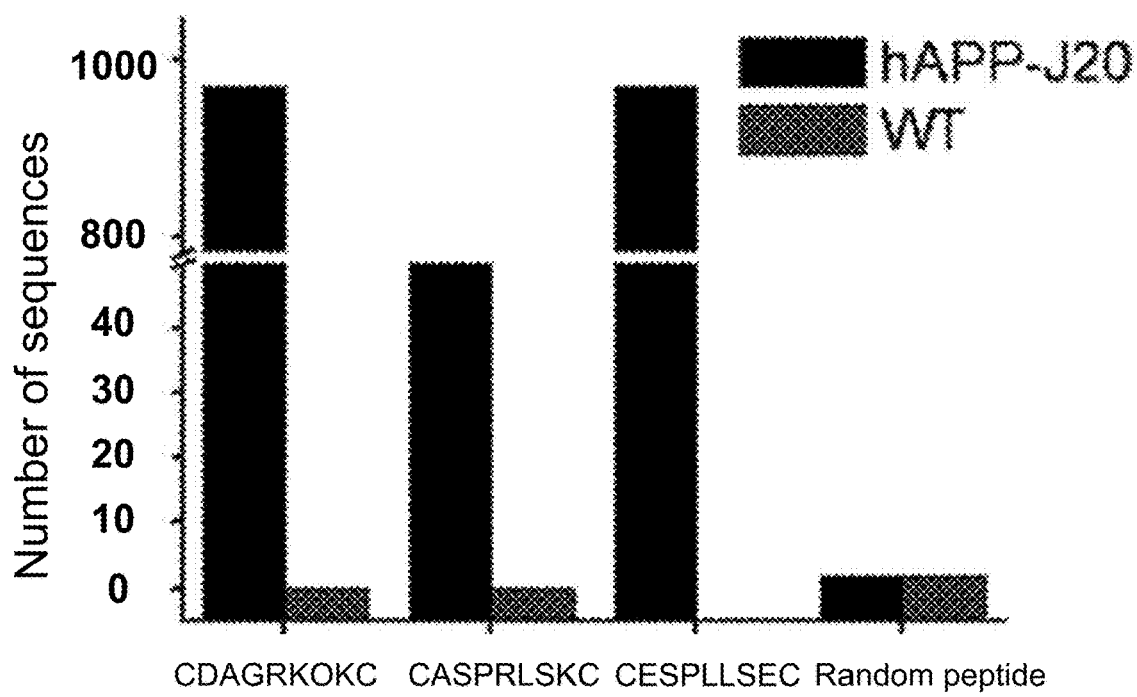
FIG. 6 is a graphical representation relating to peptide sequences recovered from the hippocampus in phage library screening. Cyclic $CX_7C$ library was intravenously injected to hAPP-J20 mice and wild-type (WT) littermate mice at 9 months of age. After 30 min, the mice were perfused and phages were recovered from the hippocampus. Phage insert DNA was subjected to high-throughput sequencing. Comparison of the number of the most common insert sequences in the phage pools recovered from the hAPP-J20 and WT mice is shown.

High throughput sequencing analysis of the peptide-encoding region of the phage genome revealed peptide sequences that were highly enriched in the phage pools from the 9-month-old hAPP-J20 mice (FIG. 6). Consensus motif analysis across all of the age groups further showed that one sequence motif, SEQ ID NO: 101, was enriched in all hAPP-J20 age groups, but absent in the WT controls (FIG. 2). One of the peptides in the 9-month phage pool CDAGRKQKC (SEQ ID NO: 102; "DAG") agreed with the consensus sequence and contained the most commonly occurring amino acids in the surrounding positions (data not shown). Subsequent analyses was focused on the DAG peptide because intravenously injected DAG appeared to home to the hAPP-J20 mouse brain at all stages, from onset at 3 months through the late stages at 9 months of age.

Fluoresceinamine (FAM)-labeled synthetic DAG peptide homed from an intravenous injection to the hippocampus of 9-month-old hAPP-J20 mice, but not WT mice (data not shown). There was little if any accumulation of the peptide in other organs of the hAPP-J20 mouse except for kidney, probably due to the renal excretion of the peptide (data not shown). A control peptide for DAG, with the same overall structure and charge (+2) (CRKQGEAKC; SEQ ID NO: 103) showed essentially no homing to the hippocampus of hAPP-J20 mice of the same age (data not shown), thus, confirming DAG specificity for the hAPP-J20 brain. The same specificity of DAG for AD was observed in the Tg2576 model (data not shown). In this case, the signal from DAG was detected both in the hippocampus and in the cortex.

Further examination suggested that DAG labeled stellar-shaped glial cells adjoining blood vessels, and also partially co-localized with CD31-positive endothelial cell staining. The Tg2576 model showed more pronounced endothelial localization of DAG than hAPP-J20 (data not shown).

DAG Targets Activated Astrocytes in AD Mice

To identify the cellular target of DAG in adult transgenic AD mouse brain, the inventors stained brain sections of DAG-injected hAPP-J20 mice with anti-GFAP (glial fibrillary acidic protein) antibody, a marker for astrocytes in this setting, and an anti-amyloid beta (Aβ) antibody. The abundance of Aβ plaques in the transgenic and their absence in the wild-type brains confirmed the advanced stage of the disease as expected of aged hAPP-J20 mice (data not shown). DAG accumulated within a subpopulation of GFAP-positive hypertrophic astrocytes surrounding the Aβ plaques suggesting its specificity for activated (reactive) astrocytes (data not shown). In AD, astrocytes are known to become reactive, particularly in the vicinity of amyloid plaques. In addition to astrocyte cell bodies, extracellular DAG accumulated in proximity to astrocytes (data not shown). A similar pattern of both cellular and extracellular accumulation of DAG was observed in the brains of Tg2576 mice injected intravenously with FAM-DAG (data not shown).

The affinity of DAG for hAPP-J20 mouse astrocytes was confirmed by ex vivo peptide binding to brain sections in an overlay assay. DAG bound to a much greater degree in the hippocampal region of hAPP-J20 mice than to age-matched wild-type mice (data not shown). As observed for in vivo homing, DAG binding associated with GFAP positive astrocytes surrounding Aβ plaques.

DAG Targets vascular Changes in the Cerebrocortex

The strong vascular accumulation of DAG seen in the Tg2576 model was further evaluated. Immunostaining on brain sections of DAG-injected Tg2576 mice showed significant colocalization of DAG with Aβ and CD31 (data not shown). Previous studies have shown that a subset of Aβ peptides localize to small blood vessels in AD brain, contributing to cerebral amyloid angiopathy (CAA). This phenomenon is reported to be particularly pronounced in aged Tg2576 mice. The data agree with those observations and show that DAG targets Aβ-positive vessels in these mice.

DAG Receptor Identified as Connective Tissue Growth Factor (CTGF)

Figure 7:
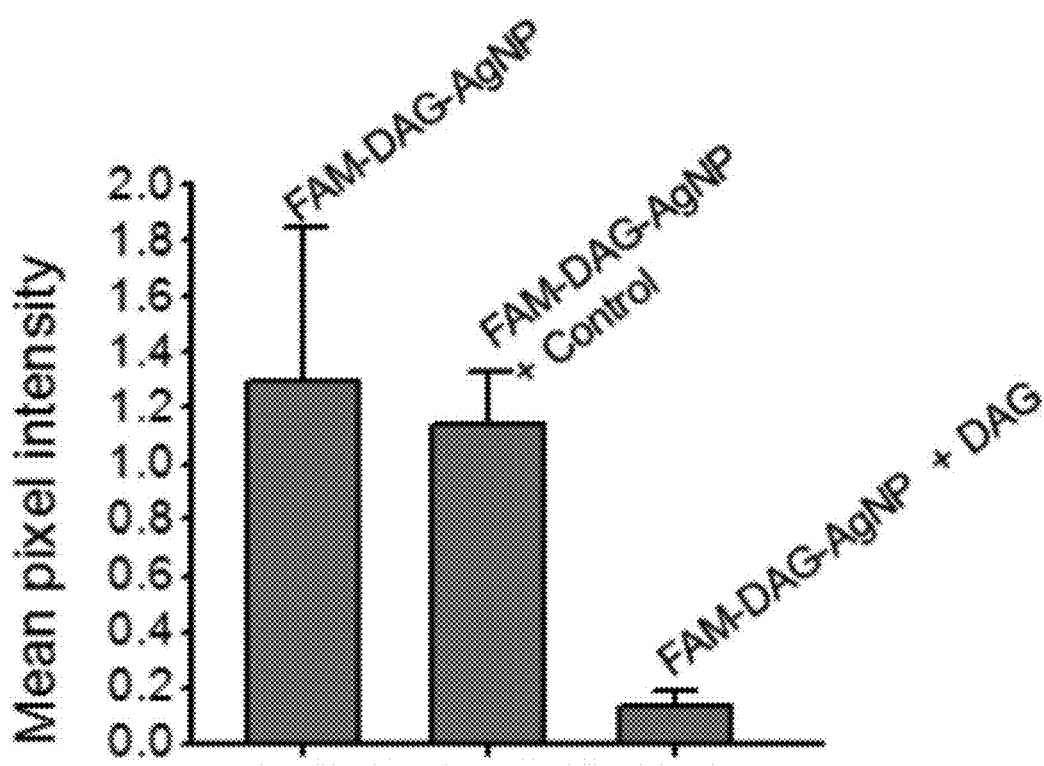
FIG. 7 is a graphical representation showing quantity of DAG-coated silver nanoparticles (DAG-AgNPs) binding to human astrocytoma U251 cells. Cultured U251 cells were incubated with DAG-AgNPs alone, in the presence of free non-labeled control peptide, or an excess of free, non-labeled DAG (both at 200 µM), for 1 hour at 37° C. Nanoparticle binding was quantified from fluorescence micrographs using ImageJ™ software. Scale bar, 20 µm.

To isolate the receptor for DAG, an astrocytoma cell line (U251) was identified that exhibited binding of DAG peptide. DAG-conjugated silver nanoparticles (DAG-AgNP) bound robustly to these cells, much more so than non-targeted nanoparticles (FIG. 7). The binding of DAG-AgNP to the U251 cells was specific, as it was inhibited by co-incubation with an excess of free, non-labeled DAG (FIG. 7).

Figure 8:
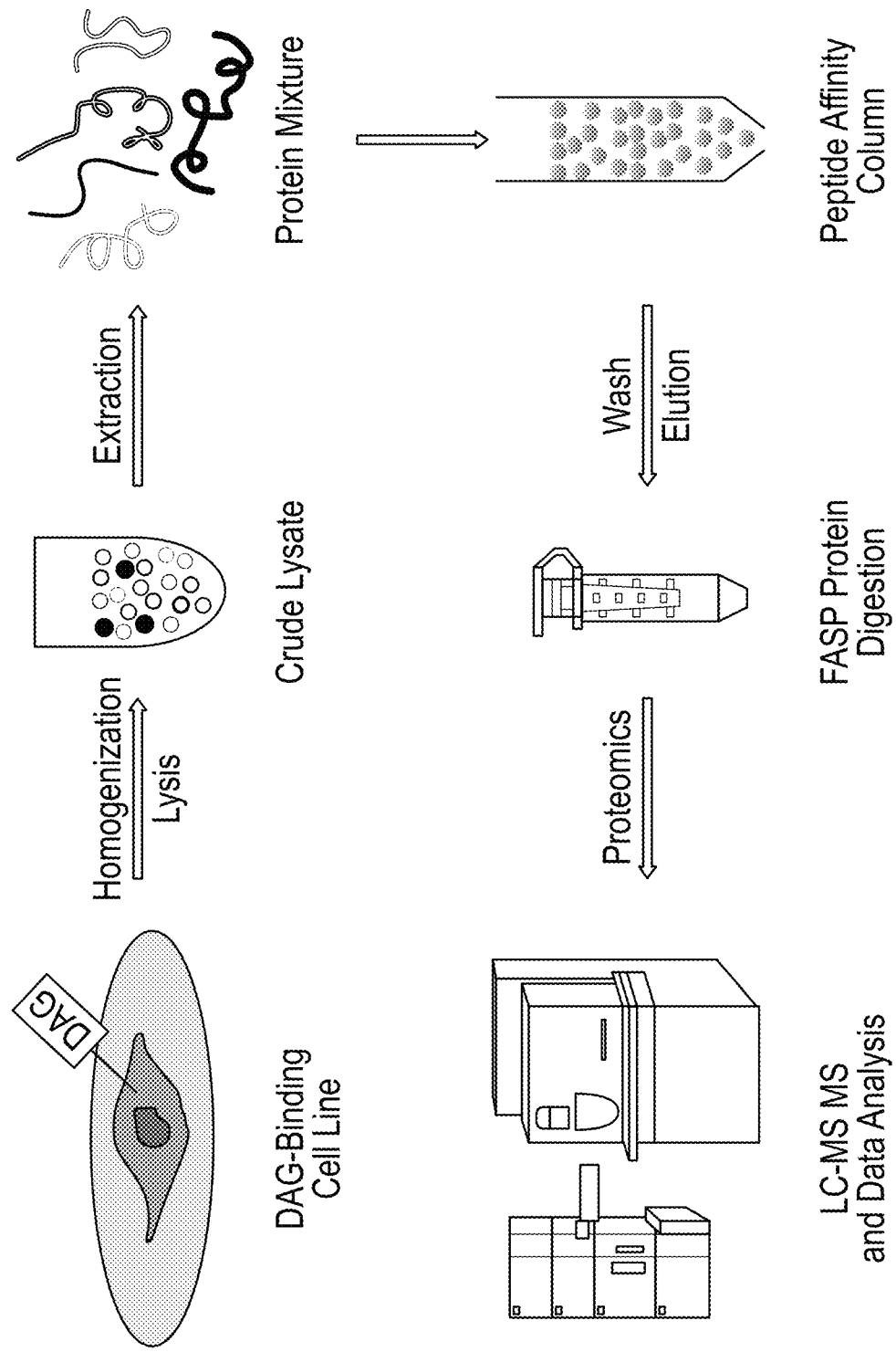
FIG. 8 is a schematic for identification of DAG receptor from a DAG-binding cell line.
Figure 9A:
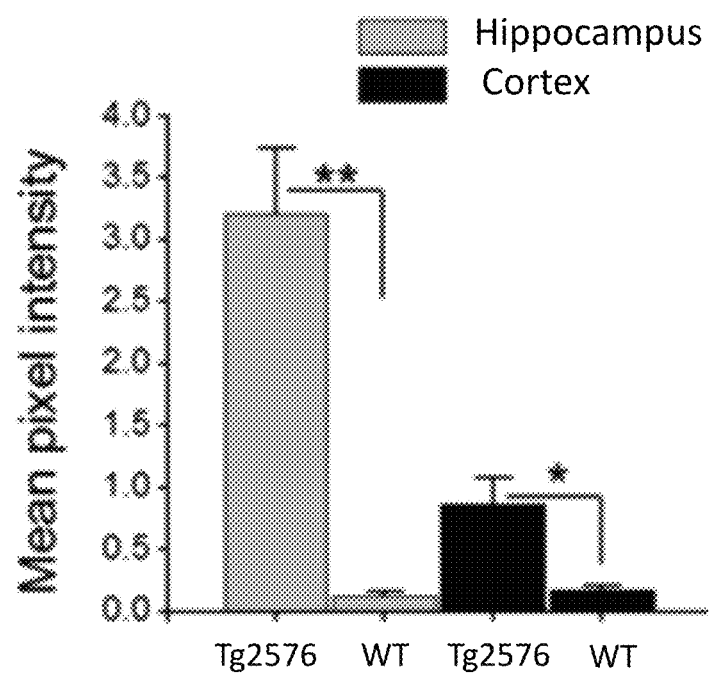
FIGS. 9A-9B is a series of graphs showing overexpression of CTGF in mouse models of AD.
Figure 9B:
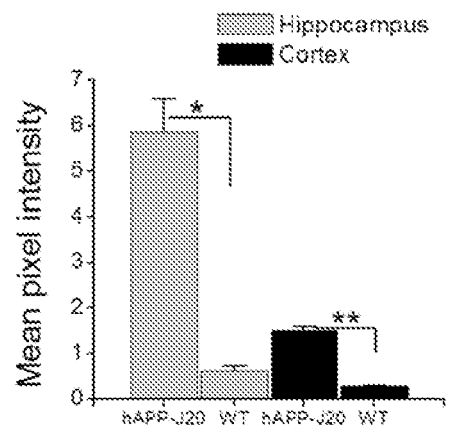

Next, U251 cell lysates were used for affinity chromatography separation on a DAG-affinity matrix (schematic in FIG. 8). Mass spectrometry on the fraction eluted with free DAG peptide revealed a number of hits, one of which was CTGF (also referred to as CCN2). CTGF is a member of the CCN family of matricellular proteins that is induced in inflammation and tissue repair. Next, CTGF expression was analyzed in mouse brains and significantly higher CTGF expression was noted in hippocampus and cerebrocortex of hAPP-J20 and Tg2576 mice than WT mice (FIG. 9). The elevated CTGF expression was associated with GFAP-positive astrocytes in the transgenic mice (data not shown). In both AD transgenic mouse models, DAG strongly homed to CTGF-positive areas localizing in stellate shaped structures characteristic of astrocytes (data not shown).

Figure 10:
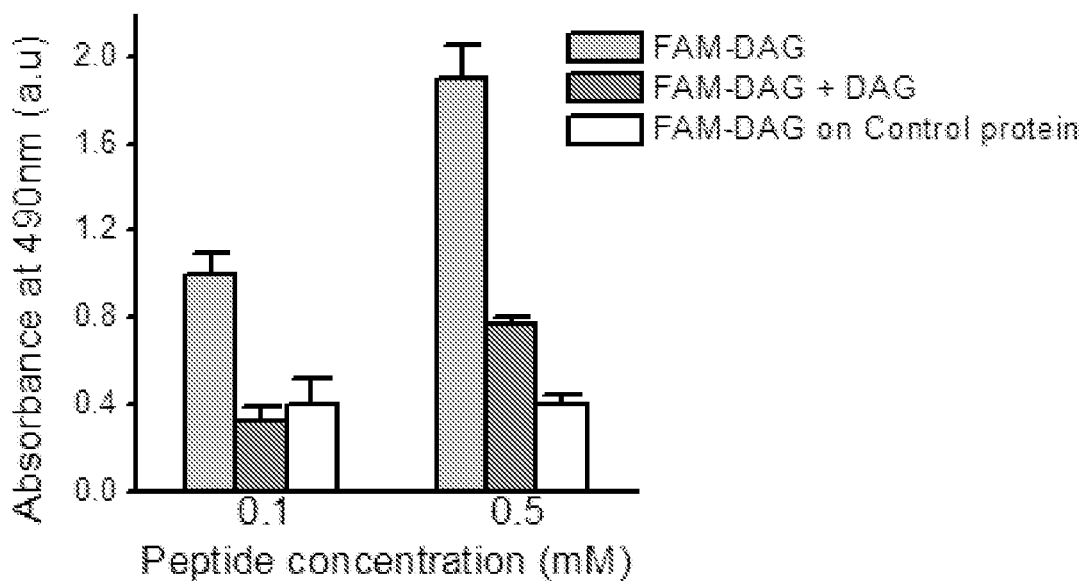
FIG. 10 is a graphical representation relating to identification of a receptor for DAG. DAG binds to recombinant CTGF. FAM-DAG was incubated on ELISA plate coated with recombinant human CTGF at two different peptide concentrations of the FAM peptide alone (light gray bars), or in the presence of non-labeled DAG (0.5 mM) (dark gray bars). The background binding of DAG to albumin (BSA) used as a control protein did not change with concentration of peptide (open bars). Non-labeled DAG inhibited the binding of FAM-DAG, demonstrating specificity of the CTGF binding. DAG was also shown to colocalize with CTGF. FAM-DAG was intravenously injected in 9-month-old hAPP-J20 and WT mice, allowed to circulate for 30 minutes, after which mice were perfused, and the brains were fixed, sectioned and stained for FAM (green) and CTGF (red).

To further validate CTGF as a DAG receptor, in vitro binding of DAG to recombinant human CTGF was tested. DAG bound to CTGF-coated plates in a dose-dependent manner (FIG. 10). There was only minimal binding to a control protein (BSA), with no increase in binding with increasing peptide concentration. Furthermore, DAG binding to CTGF was inhibited in the presence of an excess of unlabeled DAG, confirming the specificity. These data indicate that CTGF is the DAG receptor in AD brain.

DAG Detects Vascular Changes in Early AD

Figure 11:
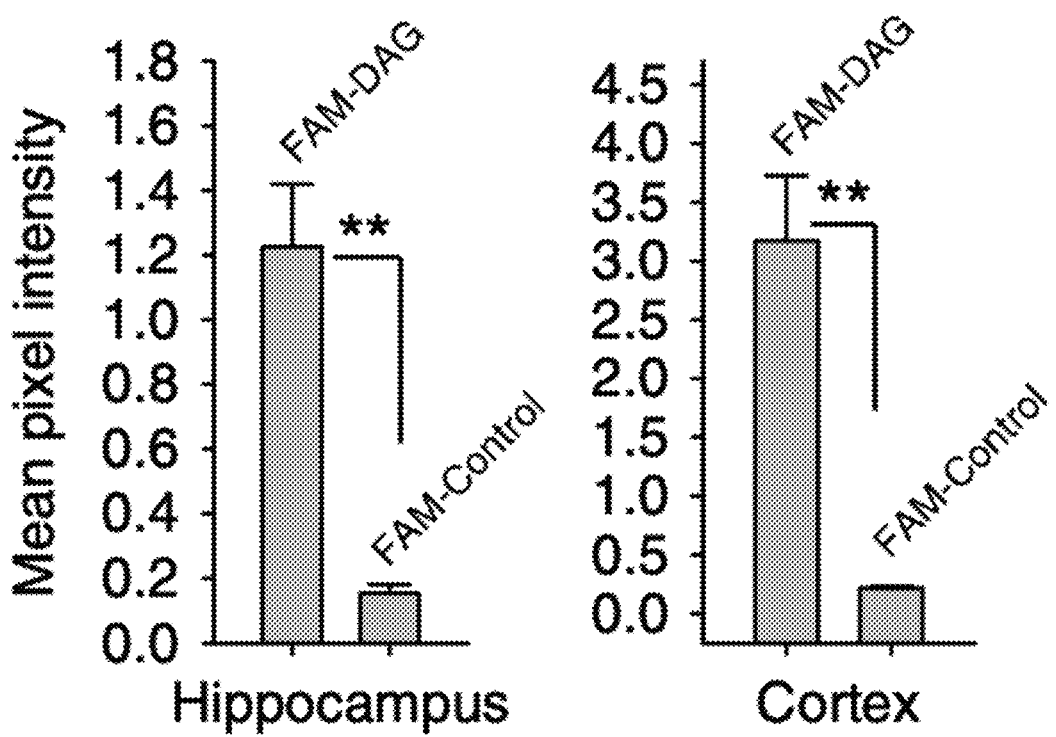
FIG. 11 is a graphical representation pertaining to DAG homing to early stage hAPP-J20 mouse brain. DAG co-localizes with GFAP. FAM-DAG or control peptide were intravenously injected to 3-4 month old hAPP-J20 mice and allowed to circulate for 30 min. The mice were perfused, and brains were fixed, sectioned and stained for FAM (green). The signal from FAM was quantified using ImageJ™ and plotted in bar graph as shown. DAG also co-localizes with CTGF and blood vessels. DAG was injected intravenously to 3-4 month old J20 mice, and the sections were stained for FAM (green), CTGF, GFAP, and CD31. The blood vessels lacked detectable Aβ accumulation.

As the DAG peptide was originally identified from phage screening that spanned different ages of the J20 mice, DAG homing in hAPP-J20 mice with early-stage AD (3-4 months of age) was next tested. Robust DAG homing in young hAPP-J20 animals was observed, mostly in the cerebrocortex and the hippocampus (FIG. 11). At this age, DAG homing was predominantly found in blood vessels, co-localizing with CD31. Additionally, the peptide signal co-localized with GFAP-positive cells suggesting that it also targeted astrocytes in the neurovascular unit (data not shown). The vessels were also positive for CTGF. Importantly, in agreement with prior reports, no Aβ deposition at this early stage in this AD mouse model was observed, showing that DAG homing is independent of the presence of detectable amyloid deposits.

DAG Binds Specifically to Human AD Samples

Figure 12A:
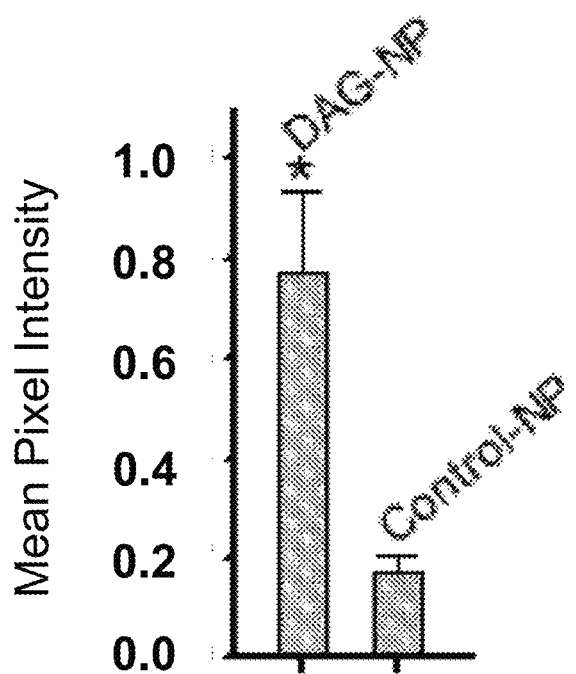

Mouse AD models only go so far in mimicking the human disease, so it was important to test the peptides for their ability to recognize human AD samples. It was found that DAG-AgNP showed high binding to BBB-type microvascular endothelial cells (BMECs) differentiated from human induced pluripotent stem cells (hiPSCs) that had been derived from AD patient fibroblasts (FIG. 12A). This binding was specific as it was inhibited by the presence of free DAG peptide (FIG. 12B). As a control, DAG peptide did not bind to hiPSC-derived BMECs from a non-demented individual (not shown). Ex vivo binding of DAG to sections from an AD human patient brain was also tested. DAG peptide bound strongly to the hippocampal region, which also displayed abundant in Aβ oligomeric plaques (data not shown), whereas control peptide showed minimal binding. Strong CTGF immunoreactivity in the hippocampus in these sections (data not shown) was also observed. Moreover, DAG binding to these sections was partially inhibited by pre-incubation with anti-CTGF antibody (data not shown), confirming the specificity of DAG binding to CTGF.

DAG Homing in Other Models of Neuroinflammation

Since DAG targets activated astrocytes in AD, in vivo homing of systemically injected DAG was tested in other models of neuroinflammation. Strong tumor homing of DAG was seen in P13 model of angiogenic glioblastoma, where the peptide co-localized with a subset of the GFAP-positive cells (data not shown). Similarly, in a model of acute penetrating brain injury, DAG injected 6 hours after injury robustly homed to the perilesional area containing activated hypertrophic astrocytes (data not shown). Lastly, DAG also accumulated in GFAP-positive astrocytes in mTHY-1/α-synuclein overexpressing mouse model of Parkinson's disease (data not shown). Additionally, immunohistochemical analysis showed significantly higher CTGF expression in brain sections from a patient with Parkinson's disease than normal brain (data not shown). Collectively, these data suggest that DAG targets activated astrocytes in both acute and chronic models of neuroinflammation.

Discussion

The application of in vivo phage display in mouse models of AD for identification of peptides that target components of the neurovascular unit is described. One of the peptides, DAG, selectively recognizes a subset of astrocytes that are activated in AD starting at an early stage of the disease. The inventors also show that the peptide recognizes activated astrocytes in other models of neuroinflammation. Importantly, the target of this peptide is expressed both in mouse and human AD brain.

This is the first application of in vivo phage display to probe for specific, systemically-accessible molecular signatures present in the AD brain. The higher number of phage recovered from brains of aged hAPP-J20 mice compared to age-matched normal mice and younger hAPP-J20 mice is consistent with the notion of a leaky BBB in late stages of the disease. Vascular impairment represents an important factor in the pathology of AD, particularly with dysfunction of components of the neurovascular unit, and disruption of the BBB has been widely reported in animal models of AD, as well as patients with late-stage AD. Increased permeability of the BBB apparently allows the phage to enter the subarachnoid space, which is normally not accessible, consequently with some phage binding to specific extravascular targets. The DAG peptide identified in the screen shows binding and accumulation in brain endothelia as well as in the brain parenchyma.

Binding of the DAG peptide to components of the neurovascular unit (in this case, endothelial cells and astrocytes) in AD brain is of particular interest, as it suggests DAG recognizes a signature present in AD, which can be readily accessed through the systemic circulation. Importantly, vascular homing of DAG appears to be independent of the BBB status. DAG homing to the neurovascular unit in hAPP-J20 mice at an early stage of the disease, when the BBB is presumably still intact, supports that conclusion. Vascular alterations in AD have been reported, even at early stages of the disease. Moreover, early in the disease, neuroinflammation and synaptic/neuronal loss precede Aβ plaque deposition and tau tangle formation, hallmarks of late stage AD. The data showing DAG homing to early stage AD in the hAPP-J20 mouse model indicate that the peptide recognizes an early change in the neurovascular niche.

It was important to rule out the possibility that BBB leakage was the reason for the in vivo brain accumulation of DAG in the AD mice. It was found that the binding of the peptide to brain sections was independent of access through the BBB. DAG binding to hAPP-J20 brain sections was far stronger than DAG binding to WT brain or a control peptide binding to hAPP-J20 brain. These results suggest that upregulation of the DAG target molecule is a factor in the preferential homing of systemically injected DAG to AD brain. While BBB permeability is likely needed for DAG to reach extravascular targets, the blood vessels should be available for DAG binding regardless of the status of the BBB. The results on the DAG target molecule discussed below confirm these conclusions.

This study provides evidence that CTGF is the target molecule for DAG. CTGF is a matricellular protein that acts as a regulator of several cellular functions, including cell adhesion, migration, mitogenesis, differentiation, and survival. CTGF was one of several candidate proteins that was identified from DAG affinity chromatography, and the inventors focused on it as a candidate receptor for DAG because high CTGF expression has been reported in activated astrocytes in the brains of human AD patients. High CTGF expression was also found in AD brains, both human and mouse. In addition, it was found that the endothelial cells and adjoining astrocytes in hAPP-J20 mouse brain were positive for CTGF immunostaining, in agreement with the observation of accumulation of systemically injected DAG in these cells. Further evidence for CTGF as the DAG receptor includes direct binding of FAM-labeled DAG to recombinant CTGF and inhibition of the binding with unlabeled DAG. Moreover, the binding of CTGF to extracellular matrices creates an insoluble fraction of the growth factor that can immobilize the peptide binding to it. Based on these data, it is concluded that CTGF is the receptor for DAG.

Since the DAG peptide was initially identified using mouse models of AD, it was important to determine if the peptide also recognizes the human AD tissue. The results show that in fact it does. First, DAG binds to human CTGF, as shown by the binding of DAG to the U251 human astrocytoma cells that was used as the source of stating material for the identification of CTGF as the DAG receptor. Second, the recombinant CTGF that was used to show the binding of DAG to CTGF was of human origin. Third, DAG specifically bound to human AD iPS cells differentiated into BBB-type endothelial cells. Finally, DAG bound to human AD brain sections in an overlay assay. Taken together with the demonstration of elevated CTGF expression in human AD brain, these results show that DAG is relevant to human AD.

Studies have reported CTGF up-regulation in patients with other neuroinflammatory conditions, such as Parkinson's disease, brain injury, glioblastoma, and cerebral infarction. Given its potential to modulate the cellular phenotype and remodel tissue in the CNS following injury and in neurodegenerative disease, CTGF may represent an attractive therapeutic target. The fact that DAG homes to brain in animal models of Parkinson's disease, brain injury, and glioblastoma agrees with the published CTGF expression pattern and suggests that DAG has the potential for broad applicability in brain diseases. For example, imaging applications are envisioned, in which the differential diagnosis could be based on the pattern of accumulation of the DAG-guided contrast agent. A particularly attractive potential application of DAG would be as a biomarker for early detection of AD, as suggested by DAG homing to AD brain vessels at early stages of disease in the hAPP-J20 mouse model.

In conclusion, the DAG peptide provides a tool for targeting of the neurovascular unit to improve imaging and management of neuroinflammatory conditions and/or neurodegenerative conditions. It also draws attention to the potential role of CTGF in AD and other neurological diseases, which heretofore has been essentially unexplored.

EXAMPLE 3

Anti-CTGF Antibody Binding in Alzheimer's Disease Mice

To determine targeting of anti-CTGF antibody in AD mice, 50 microgram of antibody against connective tissue growth factor (CTGF) (Rabbit polyclonal purchased from Invitrogen #PA1-22376) was injected intravenously in 18 month-old Tg2576 transgenic mice. The mice were perfused after 1 hour of circulation and then the brains were collected and distribution of the antibody was visualized in the brain. It was noticed that the CTGF specific antibody localized in the hippocampus of the AD mice. This signal showed a star shaped pattern and strongly co-localized with glial fibrillary protein (GFAP) positive staining for activated astrocytes. It has been shown that patients with AD express glia specific genes, such as GFAP, in the hippocampus. In the control experiment, a control rabbit IgG antibody (50 ug) was injected in Tg2576 mice of same age. There was no specific targeting observed to the hippocampus with the rabbit IgG. In summary, the anti-CTGF antibody localized in the hippocampus of AD mice and co-localized with GFAP staining. The anti-CTGF antibodies used herein are merely illustrative and any antibody that binds to CTGF or antigenic fragments thereof could be used.

EXAMPLE 4

DAG Peptide MRI Imaging in J20 Mice

MRI experiments using dextran coated pegylated iron oxide nanoworms conjugated with DAG peptide were conducted to demonstrate imaging application of DAG peptide. DAG-coated iron oxide nanoworms were intravenously injected (5 mg/kg) into J20 AD model mice and age-matched wild-type littermates and imaged after 5 hours on a 7T scanner. Hypointense signal (dark punctate spots) was detected in the brains of the AD mice ex vivo, after perfusion to remove excess nanoworms from circulation (FIG. 13a). This signal is absent in the WT animal (FIG. 13b) suggesting that the signal is specific for AD mice.

Although the invention has been described with reference to the above examples, it will be understood that modifications and variations are encompassed within the spirit and scope of the invention. Illustrative examples of the invention are attached herein as Exhibits A and B which are herein incorporated by reference in their entireties. Accordingly, the invention is limited only by the following claims.

What is claimed is:

1. A composition comprising a peptide comprising the amino acid sequence of SEQ ID NO: 11 or SEQ ID NO: 102 conjugated to a therapeutic agent.

2. The composition of claim 1, wherein the peptide comprises the amino acid sequence as set forth in SEQ ID NO: 11 (CESPLLSEC).

3. The composition of claim 1, wherein the peptide comprises the amino acid sequence as set forth in SEQ ID NO: 102 (CDAGRKQKC).

4. The composition of claim 1, wherein the peptide is recombinant or synthetic.

5. The composition of claim 1, wherein the peptide comprises a non-natural amino acid.

6. A composition comprising a peptide comprising the amino acid sequence of SEQ ID NO: 11 or SEQ ID NO: 102 conjugated to a detection moiety.

7. The composition of claim 6, wherein the peptide has the amino acid sequence as set forth in SEQ ID NO: 11 (CESPLLSEC).

8. The composition of claim 6, wherein the peptide has the amino acid sequence as set forth in SEQ ID NO: 102 (CDAGRKQKC).

9. The composition of claim 6, wherein the peptide is recombinant or synthetic.

10. The composition of claim 6, wherein the peptide comprises a non-natural amino acid.

11. An isolated peptide comprising the amino acid sequence of SEQ ID NO: 11 or SEQ ID NO: 102, wherein the peptide comprises a non-natural amino acid.

12. The isolated peptide of claim 11, wherein the peptide has an amino acid sequence as set forth in SEQ ID NO: 11 (CESPLLSEC).

13. The isolated peptide of claim 11, wherein the peptide has an amino acid sequence as set forth in SEQ ID NO: 102 (CDAGRKQKC).

\* \* \* \* \*

SEQUENCE LISTING

```
<160> NUMBER OF SEQ ID NOS: 131

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
      and is 0 to 8 amino acids
<220> FEATURE:
<221> NAME/KEY: misc_feature
<222> LOCATION: (2)..(2)
<223> OTHER INFORMATION: Xaa can be Gly or Ala
<220> FEATURE:
<221> NAME/KEY: misc_feature
<222> LOCATION: (3)..(3)
<223> OTHER INFORMATION: Xaa can be Lys or His or Arg
<220> FEATURE:
<221> NAME/KEY: misc_feature
<222> LOCATION: (4)..(4)
<223> OTHER INFORMATION: Xaa can be Lys or His or Arg
<220> FEATURE:
<221> NAME/KEY: misc_feature
<222> LOCATION: (5)..(5)
<223> OTHER INFORMATION: Xaa can be Asn or Gln
<220> FEATURE:
<221> NAME/KEY: misc_feature
<222> LOCATION: (6)..(6)
<223> OTHER INFORMATION: Xaa can be any naturally occurring amino acid
      and is 0 to 8 amino acids

<400> SEQUENCE: 1

Xaa Xaa Xaa Xaa Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Cys Ser Lys Thr Thr Glu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Cys Glu Gln Val Arg Gln Lys Arg Cys
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

Cys Glu Gln Val Arg Gln Lys Arg Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Cys Asn Ser Lys Glu Thr Ser Arg Cys
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic

<400> SEQUENCE: 6

Cys Ser Pro Glu
1

<210> SEQ ID NO 7
<211> LENGTH: 9
<212> TYPE: PRT
<213> ORGANISM: Artificial Sequence
<220> FEATURE:
<223> OTHER INFORMATION: Synthetic

<400> SEQUENCE: 7

Cys Leu Thr Asp Asn Glu Glu Thr Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Cys Gln Gly Pro Arg Pro Val Lys Cys
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic

<400> SEQUENCE: 9

Ser Ser Val Asp Lys Leu
1               5
```

```
<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Cys Thr Lys Thr Ala Lys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Cys Glu Ser Pro Leu Leu Ser Glu Cys
1               5

<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Cys Glu Ser Asn
1

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Cys Gly Asp Thr Lys Ile Gly Lys Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Cys Asp Pro Ser Asp Thr Asn Val Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Cys Arg Pro Val Ile Lys Ala Asn Cys
1               5
```

```
<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Cys Gly Lys Lys Ser Thr Glu Gly Cys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic

<400> SEQUENCE: 17

Cys Arg Thr Val Lys Arg
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Cys Arg Gln Gly Asn Lys Lys Gln Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Cys Ala Thr Glu Gln Val Val Glu Cys
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic

<400> SEQUENCE: 20

Cys Gln Tyr Asn Lys Thr Asn Gly Ala Lys Leu
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic

<400> SEQUENCE: 21

Cys Arg Val Gln Lys Ser Gly Leu Ala Lys Leu
1               5                   10
```

```
<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Ala Gly Gly Leu Asp Asp Ser Val Leu Ser Leu
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic

<400> SEQUENCE: 23

Cys Ala Ser Pro Cys
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Cys Thr Ser Met Arg Lys Pro Gly Cys
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Cys Gly Ala Asp Glu Glu Ile Cys
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic

<400> SEQUENCE: 26

Cys Ser Arg Ser Asn Asp
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic

<400> SEQUENCE: 27

Cys Glu Glu Gln Leu Tyr Ser Gly Ala Lys Leu
1               5                   10
```

```
<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Cys Thr Gly Gly Lys Ser Ser Ser Cys
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Cys Arg Arg Lys Thr Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Cys Ala Gln Leu Ala Glu Ala Arg
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic

<400> SEQUENCE: 31

Cys Gln Asn Ser Arg Arg Ser Asn Cys
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Cys Asp Thr Val Ser Lys
1               5

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Cys Ala Glu Gly Arg Arg Val Ser Ala Lys Leu
1               5                   10
```

```
<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Cys Asp Pro Ser Asp Thr Asn Val Leu Leu Ser Leu
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic

<400> SEQUENCE: 35

Cys Asp Arg Thr Gln Arg Thr Ala Lys Leu
1               5                   10

<210> SEQ ID NO 36
<211> LENGTH: 4
<212> TYPE: PRT
<213> ORGANISM: Artificial Sequence
<220> FEATURE:
<223> OTHER INFORMATION: Synthetic

<400> SEQUENCE: 36

Cys Glu Asp Glu
1

<210> SEQ ID NO 37
<211> LENGTH: 10
<212> TYPE: PRT
<213> ORGANISM: Artificial Sequence
<220> FEATURE:
<223> OTHER INFORMATION: Synthetic

<400> SEQUENCE: 37

Ser Cys Arg Lys Thr Pro Glu Lys Lys Cys
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

Cys Lys Gly Ser Gly Leu Lys Thr Cys
1               5

<210> SEQ ID NO 39
<211> LENGTH: 9
<212> TYPE: PRT
<213> ORGANISM: Artificial Sequence
<220> FEATURE:
<223> OTHER INFORMATION: Synthetic

<400> SEQUENCE: 39

Cys Ser Val Gly Arg Thr Val Lys Cys
1               5
```

```
<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Cys Ala Lys Leu Ala Lys Gly Cys
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic

<400> SEQUENCE: 41

Cys Ala Lys Leu Arg Ala Ala Ala Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Cys Leu Ser Thr Lys Thr Lys Thr Cys
1               5

<210> SEQ ID NO 43
<211> LENGTH: 4
<212> TYPE: PRT
<213> ORGANISM: Artificial Sequence
<220> FEATURE:
<223> OTHER INFORMATION: Synthetic

<400> SEQUENCE: 43

Cys Leu Gln Lys
1

<210> SEQ ID NO 44
<211> LENGTH: 9
<212> TYPE: PRT
<213> ORGANISM: Artificial Sequence
<220> FEATURE:
<223> OTHER INFORMATION: Synthetic

<400> SEQUENCE: 44

Cys Lys Pro Ala Pro Asn Gln Lys Cys
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Cys Thr Val Lys Leu Ser Arg Thr Cys
1               5
```

```
<210> SEQ ID NO 46
<211> LENGTH: 9
<212> TYPE: PRT
<213> ORGANISM: Artificial Sequence
<220> FEATURE:
<223> OTHER INFORMATION: Synthetic

<400> SEQUENCE: 46

Cys Gly Ile Glu Val Arg Glu Asp Cys
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic

<400> SEQUENCE: 47

Cys Lys Asn Gly Gly Thr Ala Val Cys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Cys Ala His Pro Ala Arg Thr Lys Cys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Cys Gly Leu Gly Arg Val Thr Lys Cys
1               5

<210> SEQ ID NO 50
<211> LENGTH: 4
<212> TYPE: PRT
<213> ORGANISM: Artificial Sequence
<220> FEATURE:
<223> OTHER INFORMATION: Synthetic

<400> SEQUENCE: 50

Cys Ala Gly Asp
1

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

Cys Pro Gln Asn Gln Arg Val Lys Cys
1               5
```

```
<210> SEQ ID NO 52
<211> LENGTH: 6
<212> TYPE: PRT
<213> ORGANISM: Artificial Sequence
<220> FEATURE:
<223> OTHER INFORMATION: Synthetic

<400> SEQUENCE: 52

Cys Ser Lys Leu Ser Arg
1               5

<210> SEQ ID NO 53
<211> LENGTH: 10
<212> TYPE: PRT
<213> ORGANISM: Artificial Sequence
<220> FEATURE:
<223> OTHER INFORMATION: Synthetic

<400> SEQUENCE: 53

Ser Cys Glu Asp Thr Val Arg Val Gly Cys
1               5                   10

<210> SEQ ID NO 54
<211> LENGTH: 6
<212> TYPE: PRT
<213> ORGANISM: Artificial Sequence
<220> FEATURE:
<223> OTHER INFORMATION: Synthetic

<400> SEQUENCE: 54

Cys Ala Asp Gly Arg Leu
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic

<400> SEQUENCE: 55

Cys Ala Arg Pro Asp Lys Glu Glu Cys
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic

<400> SEQUENCE: 56

Cys Glu Arg Leu Thr Ser Ala Gly Cys
1               5

<210> SEQ ID NO 57
<211> LENGTH: 5
<212> TYPE: PRT
<213> ORGANISM: Artificial Sequence
<220> FEATURE:
<223> OTHER INFORMATION: Synthetic

<400> SEQUENCE: 57

Cys Ser Lys Ser Val
1               5
```

```
<210> SEQ ID NO 58
<211> LENGTH: 9
<212> TYPE: PRT
<213> ORGANISM: Artificial Sequence
<220> FEATURE:
<223> OTHER INFORMATION: Synthetic

<400> SEQUENCE: 58

Cys His Ser Asn His Glu Ser Asp Cys
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic

<400> SEQUENCE: 59

Cys Asp Arg Lys Asp Asp Ile Val Cys
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic

<400> SEQUENCE: 60

Cys Asn Gly Glu Gly Lys Arg Gly Cys
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic

<400> SEQUENCE: 61

Cys Pro Arg Val Leu Lys
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Cys Asp Ala Arg Leu Lys Arg Gly Cys
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic

<400> SEQUENCE: 63

Cys Ala Leu Arg Asp Gly Asp Ile Cys
1               5
```

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Cys Arg Gly Pro Ser Asp Lys Gly Cys
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Cys Asn Lys Ala Pro Thr Thr Arg Cys
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

Cys Gly Asp Arg Lys Gly Pro Arg Cys
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic

<400> SEQUENCE: 67

Cys Leu Ala Met Val Glu Ala Asp Cys
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Cys His Val Arg Thr Asp Asp Pro Cys
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

Cys Ala Arg Glu Ser Asn Lys Lys Cys
1               5

```
<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Cys Ser Ser Arg Arg Ser Thr Gly Cys
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic

<400> SEQUENCE: 71

Cys Lys Ala Gly Asp Asp Asn Ser Cys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic

<400> SEQUENCE: 72

Cys Arg Lys Arg Asp Ser Gly Arg Cys
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Cys Lys Pro Leu Ala Asn Asp Asn Cys
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic

<400> SEQUENCE: 74

Cys Leu Gly Arg Arg Glu Lys Asp Cys
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

Cys His Arg Asp Ala Lys Gly Gly Cys
1               5
```

```
<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Cys Thr Ala Gln Ser Pro Pro Ala Cys
1               5

<210> SEQ ID NO 77
<211> LENGTH: 8
<212> TYPE: PRT
<213> ORGANISM: Artificial Sequence
<220> FEATURE:
<223> OTHER INFORMATION: Synthetic

<400> SEQUENCE: 77

Cys Arg Arg Pro Met Ala Gln Cys
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic

<400> SEQUENCE: 78

Cys Gly Met Lys Gly Asp Thr Cys
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic

<400> SEQUENCE: 79

Ala Gly Gly Leu Gly
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Cys Lys Ala Asn Arg Asp Thr Lys Cys
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Cys Arg Thr Ser Pro Asp Arg Gly Cys
1               5
```

-continued

```
<210> SEQ ID NO 82
<211> LENGTH: 7
<212> TYPE: PRT
<213> ORGANISM: Artificial Sequence
<220> FEATURE:
<223> OTHER INFORMATION: Synthetic

<400> SEQUENCE: 82

Cys Met Ser Glu Gly Ser Val
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic

<400> SEQUENCE: 83

Cys Ser Arg Ala Arg Ser Glu
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic

<400> SEQUENCE: 84

Cys Val Pro Lys Gly Lys Leu Val Cys
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic

<400> SEQUENCE: 85

Cys Lys Val Arg Lys Ser Glu Gly Cys
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

Cys Lys Val Arg Lys Ser Glu Gly Cys
1               5

<210> SEQ ID NO 87
<211> LENGTH: 10
<212> TYPE: PRT
<213> ORGANISM: Artificial Sequence
<220> FEATURE:
<223> OTHER INFORMATION: Synthetic

<400> SEQUENCE: 87

Cys Ala Thr Pro Arg Asp Lys Arg Thr Cys
1               5                   10
```

```
<210> SEQ ID NO 88
<211> LENGTH: 5
<212> TYPE: PRT
<213> ORGANISM: Artificial Sequence
<220> FEATURE:
<223> OTHER INFORMATION: Synthetic

<400> SEQUENCE: 88

Cys Leu Ser Leu Asp
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic

<400> SEQUENCE: 89

Cys Ser Gly Asp Met Glu Thr Lys Cys
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic

<400> SEQUENCE: 90

Cys Ser Asp Arg Arg Leu Ile Asp Cys
1               5

<210> SEQ ID NO 91
<211> LENGTH: 6
<212> TYPE: PRT
<213> ORGANISM: Artificial Sequence
<220> FEATURE:
<223> OTHER INFORMATION: Synthetic

<400> SEQUENCE: 91

Cys Ala Arg Val Lys Lys
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic

<400> SEQUENCE: 92

Cys Arg Lys Gln Pro Thr Asn Val Cys
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic

<400> SEQUENCE: 93

Cys Ser Thr Asn Ala
1               5
```

```
<210> SEQ ID NO 94
<211> LENGTH: 6
<212> TYPE: PRT
<213> ORGANISM: Artificial Sequence
<220> FEATURE:
<223> OTHER INFORMATION: Synthetic

<400> SEQUENCE: 94

Cys Ala Asp Asp Gly Cys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

Cys Arg Thr Pro Leu Asn Pro Arg Cys
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Cys Thr Arg Glu Gly Asn Glu Thr Cys
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic

<400> SEQUENCE: 97

Cys Glu Leu Ser Gln
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Cys Ser Arg Thr Ser Lys Gln Ala Cys
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic

<400> SEQUENCE: 99

Cys Thr Val Asn Gly Lys Arg Ser Cys
1               5
```

```
<210> SEQ ID NO 100
<211> LENGTH: 9
<212> TYPE: PRT
<213> ORGANISM: Artificial Sequence
<220> FEATURE:
<223> OTHER INFORMATION: Synthetic

<400> SEQUENCE: 100

Cys Ser Gly Lys Ala Gln Arg Gly Cys
1               5

<210> SEQ ID NO 101
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Gly or Ala
<220> FEATURE:
<221> NAME/KEY: misc_feature
<222> LOCATION: (2)..(2)
<223> OTHER INFORMATION: Xaa can be Lys or Arg or His
<220> FEATURE:
<221> NAME/KEY: misc_feature
<222> LOCATION: (3)..(3)
<223> OTHER INFORMATION: Xaa can be Lys or Arg or His
<220> FEATURE:
<221> NAME/KEY: misc_feature
<222> LOCATION: (4)..(4)
<223> OTHER INFORMATION: Xaa can be Asn or Gln

<400> SEQUENCE: 101

Xaa Xaa Xaa Xaa
1

<210> SEQ ID NO 102
<211> LENGTH: 9
<212> TYPE: PRT
<213> ORGANISM: Artificial Sequence
<220> FEATURE:
<223> OTHER INFORMATION: Synthetic

<400> SEQUENCE: 102

Cys Asp Ala Gly Arg Lys Gln Lys Cys
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic

<400> SEQUENCE: 103

Cys Arg Lys Gln Gly Glu Ala Lys Cys
1               5

<210> SEQ ID NO 104
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
      and is 0 to 8 amino acids
```

```
<220> FEATURE:
<221> NAME/KEY: misc_feature
<222> LOCATION: (6)..(6)
<223> OTHER INFORMATION: Xaa can be any naturally occurring amino acid
      and is 0 to 8 amino acids

<400> SEQUENCE: 104

Xaa Gly Arg Lys Gln Xaa
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic

<400> SEQUENCE: 105

Ala Lys Arg Asn Gly Lys Ser
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic

<400> SEQUENCE: 106

Gly Arg Lys Asn Val Lys Leu
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic

<400> SEQUENCE: 107

Gly Arg Lys Gln Ser Glu Arg
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic

<400> SEQUENCE: 108

Gln Gly Lys Arg Gly Thr Glu
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic

<400> SEQUENCE: 109

Gly Gly Arg Lys Gln Thr Ala
1               5
```

```
<210> SEQ ID NO 110
<211> LENGTH: 7
<212> TYPE: PRT
<213> ORGANISM: Artificial Sequence
<220> FEATURE:
<223> OTHER INFORMATION: Synthetic

<400> SEQUENCE: 110

Ala Pro Ala Gly Lys Lys Gln
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic

<400> SEQUENCE: 111

Tyr Met Gly Lys Lys Asn Ala
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic

<400> SEQUENCE: 112

Gly Leu Arg Gly Arg Arg Gln
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic

<400> SEQUENCE: 113

Lys Asp Met Gly Lys Arg Asn
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic

<400> SEQUENCE: 114

Asp Arg Gly Arg Arg Asn Pro
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic

<400> SEQUENCE: 115

Gly Gly Thr Ala Arg Arg Asn
1               5
```

```
<210> SEQ ID NO 116
<211> LENGTH: 7
<212> TYPE: PRT
<213> ORGANISM: Artificial Sequence
<220> FEATURE:
<223> OTHER INFORMATION: Synthetic

<400> SEQUENCE: 116

Ala Arg Arg Asn Thr Arg Ala
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic

<400> SEQUENCE: 117

Ala Lys Lys Asn Ala Thr Thr
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

Ser Ala Arg Lys Gln Lys Asp
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic

<400> SEQUENCE: 119

Val Ser Ala Gly Lys Arg Gln
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic

<400> SEQUENCE: 120

Arg Tyr Ala Lys Lys Asn Glu
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic

<400> SEQUENCE: 121

Arg Gly Arg Arg Asn Asp Glu
1               5
```

```
<210> SEQ ID NO 122
<211> LENGTH: 7
<212> TYPE: PRT
<213> ORGANISM: Artificial Sequence
<220> FEATURE:
<223> OTHER INFORMATION: Synthetic

<400> SEQUENCE: 122

Val Gly Asn Ala Lys Lys Gln
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic

<400> SEQUENCE: 123

Gly Lys Arg Asn Ala Arg Ser
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic

<400> SEQUENCE: 124

Ile Pro Gly Arg Lys Asn Pro
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic

<400> SEQUENCE: 125

Gly Gly Arg Arg Asn Arg Thr
1               5

<210> SEQ ID NO 126
<211> LENGTH: 7
<212> TYPE: PRT
<213> ORGANISM: Artificial Sequence
<220> FEATURE:
<223> OTHER INFORMATION: Synthetic

<400> SEQUENCE: 126

Ala Gly Lys Arg Gln Pro Met
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic

<400> SEQUENCE: 127

Gly Gly Arg Arg Asn Arg Thr
1               5
```

```
<210> SEQ ID NO 128
<211> LENGTH: 7
<212> TYPE: PRT
<213> ORGANISM: Artificial Sequence
<220> FEATURE:
<223> OTHER INFORMATION: Synthetic

<400> SEQUENCE: 128

Gly Ala Arg Arg Asn Lys Ser
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic

<400> SEQUENCE: 129

Val Ala Arg Arg Asn Val Gly
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic

<400> SEQUENCE: 130

Asp Ala Gly Arg Lys Gln Lys
1               5

<210> SEQ ID NO 131
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be Gly or Ala
<220> FEATURE:
<221> NAME/KEY: misc_feature
<222> LOCATION: (2)..(2)
<223> OTHER INFORMATION: Xaa can be Lys or Arg
<220> FEATURE:
<221> NAME/KEY: misc_feature
<222> LOCATION: (3)..(3)
<223> OTHER INFORMATION: Xaa can be Lys or Arg
<220> FEATURE:
<221> NAME/KEY: misc_feature
<222> LOCATION: (4)..(4)
<223> OTHER INFORMATION: Xaa can be Asn or Gln

<400> SEQUENCE: 131

Xaa Xaa Xaa Xaa
1
```